(12) United States Patent
Axelsson et al.

(10) Patent No.: US 9,040,637 B2
(45) Date of Patent: May 26, 2015

(54) MANGANESE COMPRISING NANOSTRUCTURES

(71) Applicant: SPAGO IMAGING AB, Stockholm (SE)

(72) Inventors: Oskar Axelsson, Höör (SE); Rodrigo M. Petoral, Jr., Lund (SE); Fredrik Ek, Lund (SE); Petter Lauritzson, Hässleholm (SE)

(73) Assignee: SPAGO IMAGING AB, Stockholm (SE)

( * ) Notice: Subject to any disclaimer, the term of this patent is extended or adjusted under 35 U.S.C. 154(b) by 0 days.

(21) Appl. No.: 14/345,461

(22) PCT Filed: Sep. 20, 2012

(86) PCT No.: PCT/EP2012/068541
§ 371 (c)(1),
(2) Date: Mar. 18, 2014

(87) PCT Pub. No.: WO2013/041623
PCT Pub. Date: Mar. 28, 2013

(65) Prior Publication Data
US 2014/0350193 A1   Nov. 27, 2014

(30) Foreign Application Priority Data

Sep. 23, 2011  (EP) ................................. 11182528

(51) Int. Cl.
*A61K 51/06* (2006.01)
*C08G 73/02* (2006.01)
(Continued)

(52) U.S. Cl.
CPC .............. *A61K 51/065* (2013.01); *A61K 49/12* (2013.01); *A61K 49/124* (2013.01);
(Continued)

(58) Field of Classification Search
None
See application file for complete search history.

(56) References Cited

U.S. PATENT DOCUMENTS 4,440,738 A * 4/1984 Fawzi et al. .................. 424/1.77
4,666,895 A * 5/1987 Bosies et al. .................. 514/108
(Continued)

FOREIGN PATENT DOCUMENTS

WO   WO-2010/135167 A1   11/2010

OTHER PUBLICATIONS

Wang et al. "The first pamidronate containing polymer and copolymer" Chem. Commum., 2006, 2795-2797.*
(Continued)

*Primary Examiner* — Robert S Loewe
(74) *Attorney, Agent, or Firm* — Harness, Dickey & Pierce, P.L.C.

(57) ABSTRACT

Disclosed herein are nanostructures comprising a polymeric framework comprising at least five geminal bisphosphonate groups, wherein the geminal bisphosphonate groups independently of each other are incorporated as —$R^3R^4C(P=O(OR^1)(OR^2))_2$, wherein $R^1$ and $R^2$ are independently selected from the group consisting of a negative charge, H, alkyl and aryl, and wherein at least one of $R^3$ and $R^4$ is a group connected to the polymeric framework with the proviso that when only one of $R^3$ and $R^4$ is such a connected group, the other of $R^3$ and $R^4$ is either a group being able to connect to the polymeric framework, or the residue of such a group, or selected from the group consisting of H, OH, $OR^5$ and $R^5$, wherein $R^5$ is a lower alkyl. The polymeric framework may comprise manganese ions. Disclosed are also methods for producing such manganese containing nanostructures, compositions comprising such manganese containing nanostructures and use of such manganese containing nanostructures, i.a. as MRI contrasting agents.

16 Claims, 5 Drawing Sheets

(51) Int. Cl.
A61K 49/12 (2006.01)
A61K 49/18 (2006.01)
B82Y 5/00 (2011.01)
B82Y 15/00 (2011.01)

(52) U.S. Cl.
CPC .......... *A61K 49/128* (2013.01); *A61K 49/1818* (2013.01); *A61K 49/1857* (2013.01); *B82Y 5/00* (2013.01); *B82Y 15/00* (2013.01); *C08G 73/0206* (2013.01); *C08G 73/0213* (2013.01)

(56) References Cited

U.S. PATENT DOCUMENTS

| | | | | |
|---|---|---|---|---|
| 4,830,847 | A | * | 5/1989 | Benedict et al. ............ 424/1.45 |
| 6,541,454 | B1 | * | 4/2003 | Breuer et al. ................ 514/16.9 |
| 6,548,042 | B2 | * | 4/2003 | Arstad et al. ................ 424/1.77 |
| 7,115,720 | B2 | * | 10/2006 | Fritzberg ........................ 534/14 |
| 7,803,891 | B2 | * | 9/2010 | Goldbach et al. ............ 526/274 |
| 7,838,625 | B2 | * | 11/2010 | Caminade et al. ............ 528/398 |
| 8,349,293 | B2 | * | 1/2013 | Corot .......................... 424/9.32 |
| 2005/0077233 | A1 | * | 4/2005 | Hedhli et al. ............ 210/500.27 |
| 2007/0106030 | A1 | * | 5/2007 | Caminade et al. ............ 525/242 |
| 2010/0022481 | A1 | * | 1/2010 | Wang et al. .................... 514/108 |
| 2010/0104506 | A1 | * | 4/2010 | Ludwig et al. ............... 424/1.11 |
| 2010/0215586 | A1 | * | 8/2010 | Port et al. ..................... 424/9.32 |
| 2010/0297025 | A1 | * | 11/2010 | Port et al. ..................... 424/9.32 |
| 2013/0296539 | A1 | * | 11/2013 | Bhushan ........................ 534/16 |

OTHER PUBLICATIONS

Tan et al. "Synthesis and Evaluation of Nanoglobular Macrocyclic Mn(II) Chelate Conjugates as Non-Gadolinium(III) MRI Contrast Agents" Bioconjugate Chem. 2011, 22, 931-937.*

Alferiev et al. "Elastomeric Polyurethanes Modified with Geminal Bisphosphonate Groups" Journal of Polymer Science: Part A: Polymer Chemistry, vol. 39, 105-116, 2001.*

Sundell et al. "Preparation of poly[ethylene-g-(vinylbenzyl chloride)] and functionalization with bis(phosphonic acid)derivatives" Reactive Polymers, 25, 1995, 1-16.*

Bulte, J. W. M., et al. (2008) "Nanoparticles in Biomedical Imaging" *Springer*, 15 pages.

Elizondo, G., et al. (1991) "Preclinical Evaluation of MnDPDP: New Paramagnetic Hepatobiliary Contract Agent for MR Imaging", *Radiology*, 178: 73-78.

Fessenden, R.J., et al. (1980) "Trends in Organosilicon Biological Research" *Advances in Organometallic Chemistry*, 18: 275-299.

Fried, J. R., (1995) "Polymer Science and Technology", *University of Cincinnati*, 3 Pages.

Grobner, T., et al. (2006), "Gadolinium—a specific trigger for the development of nephrogenic fibrosing dermopathy and nephrogenic systemic fibrosis?", *Nephrol Dial Transplant*, 21: 1104-1108.

Hanssen, R. W. J. M., et al. (2004), "The Dynamic Status Quo of Polyhedral Silsesquioxane Coordination Chemistry", *Eur. J. Inorg. Chem*, 675-683.

Hermanson, G.T., (2008), "Bioconjugate Techniques", second edition, *Elsevier*, 3 pages.

Peleshanko, S., et al. (2008) "The architectures and surface behavior of highly branched molecules", *Prog. Polym. Sci.*, 33: 523-580.

Rongved, P. (1991), "Water-soluble polysaccharides as carriers of paramagnetic contrast agents for magnetic resonance imaging: Synthesis and relaxation properties", *Carbohydrate Research*, 214: 315-323.

Sieber, M., et al. (2008), "A Preclinical Study to Investigate the Development of Nephrogenic Systemic Fibrosis: A Possible Role for Gadolinium-Based Contrast Media", *Investigative Radiology*, 43(1): 65-75.

Turetschek, K., et al. (2004), "Tumor Microvascular Changes in Antiangiogenic Treatment: Assessment by Magnetic Resonance Contrast Media of Different Molecular Weights", *Journal of Magnetic Resonance Imaging*, 20: 138-144.

Vitha, T., et al. (2009), "Gd(III) complex of a monophosphinate-bis(phosphonate) DOTA analogue with a high relaxivity; Lanthanide(III) complexes for imaging and radiotherapy of calcified tissues", *Dalton Trans.*, 3204-3214.

Adzamli, K., et al., (1997) "Preliminary Evaluation of a Polyethyleneglycol-Stabilized Manganese-Substituted Hydroxylapatite as an Intravascular Contrast Agent for MR Angiography", *JMRI*, 7(1): 204-208.

Chiariza, R. et al., (1997) "Diphonix® Resin : a Review of its Properties and Applications", *Separation Science and Technology*, 32(1-4): 1-35.

Pan, D. et al., (2008) "Ligand-Directed Nanobialys as Theranostic agent for Drug Delivery and Manganese-Based Magnetic Resonance Imaging of Vascular Targets", *J. Am. Chem. Soc.*, 130: 9186-9187.

Pan, D. et al., (2011) "Revisiting an Old Friend: Manganese-Based MRI Contrast Agents", *WIREs Nanonted Nanobiotechnol*, 3: 162-173.

Tan, M., et al. (2011) "Synthesis and Evaluation of Nanoglobular Macrocyclic Mn(II) Chelate Conjugates as Non-Gadolinium(III) MRI Contrast Agents", *Bioconjugate Chem.*, 22: 931-937.

Wang, L., et al. (2006) "The First Pamidronate Containing Polymer and Copolymer" *Chem. Commun.*, pp. 2795-2797.

International Search Report dated Oct. 15, 2012 issued in PCT Application No. PCT/EP2012/068541.

* cited by examiner y = 0.5942x - 5.2351
y = 0.0477x + 253.87

X=474 µl
P/Mg=8.89
P/Ca=6.02

MANGANESE COMPRISING NANOSTRUCTURES

PRIORITY STATEMENT

This application is a national stage application under 35 U.S.C. §371 of PCT International Application No. PCT/EP2012/068541, which has an International filing date of 20 Sep. 2012, and claims priority under 35 U.S.C. §119 to European Application No. 11182528.7 filed on 23 Sep. 2011. The contents of each application recited above are incorporated herein by reference in their entirety.

TECHNICAL FIELD OF THE INVENTION

The present invention relates to chelating polymeric nanostructures incorporating paramagnetic manganese (II) ions, as well as methods to prepare said nanostructures as well as use of the nanostructures for visualizing or imaging biological material.

BACKGROUND

Magnetic resonance Imaging, MRI, is a medical imaging modality where the soft tissues of the body are visualized by utilization of the magnetization of atomic nuclei. There are many clinical applications of the technique such as imaging of the nervous system, the vascular system and tumor imaging.

Normally the abundant hydrogen nuclei of the water molecules of the body are imaged. The strength of the MRI signal depends on the nature of the nucleus, its abundance and its local magnetic environment. These factors affect the longitudinal (T1, remagnetization time constant) and transverse (T2, signal decay time constant) relaxation times, which in turn affect the signal strength. Thus, the source of contrast in MRI is a combination of the local concentration of nuclei and their magnetic environment. Various morphological features can be enhanced by emphasizing the T1 or the T2 contrast. The local magnetic environment can be modified by the presence of contrast agents and, depending on their magnetic properties, the signal can be increased (positive contrast) or decreased (negative contrast). Positive contrast agents are often preferred because interpretation of the images becomes simpler when more brightness indicates the presence of more contrast agent. The principle of the positive contrast agents is a shortening of the longitudinal relaxation time, T1, which describes how fast the water molecules remagnetize after each scan. In the presence of a positive contrast agent more signal can be collected in a given period of time.

Furthermore, the effect of a compound on the T1 is given as the relaxivity so a high relaxivity gives a stronger signal enhancement. The relaxivity (r) is frequency dependent in a structure dependent way which complicates the comparison of data from the literature from different sources. The clinical MRI scanners usually have a magnetic field of 1.5 or 3 Tesla so we have measured our relaxivities at 1.91 T, corresponding to a proton resonance frequency of 81.3 MHz, as a reasonable compromise. Measurements may also be done at other frequencies, such as 60 MHz. The relaxivity for the commercially available gadolinium based contrast agents are close to 4/mMGd/s at the clinically relevant fields.

The market is currently dominated by water soluble gadolinium chelates. Because of their small physical size (<1 nm) they rapidly distribute into the extracellular space (the blood plus the interstitial space between the cells of the tissues) which somewhat limits the contrast effect. A problem with the in vivo use of paramagnetic metal ions, such as gadolinium, is their toxicity and the chelates in the currently marketed contrast agents rather successfully addresses this. However, recently it has been found that the chelates release small amounts of gadolinium which becomes problematic in patients with nonexistent of very poor kidney function, where a serious side effect called Nephrogenic Systemic Fibrosis, NSF, has been discovered (Grobner et al. *Nephrology, Dialysis and Transplantation* 2006, 21, 1104; Sieber et al. *Invest. Radiol.* 2008, 43, 65).

The issue of NSF brings about the question of using something other than gadolinium as a T1-shortening contrast agent; Mangafodipir is a manganese(II) chelate that has been used as a contrast agent (Elizondo, G. et al. *Radiology*, 178, 73, 1991). It has a moderate stability in vivo and much of the manganese is released as ions after injection and accumulates in the liver, giving a good contrast between healthy and cancerous tissue. The release of moderate amounts of manganese is not a major issue since it is an essential trace element for living organisms and there are mechanisms for dealing with manganese. Mangafodipir is now off the market due to poor sales volume. Manganese ions are less magnetic than gadolinium and most manganese compounds have low relaxivities, with some notable examples (Pan, D. et al. *WIREs Nanomed Nanobiotechnol*, 3, 162, 2011) showing the potential of manganese based contrast agents. If the beneficial properties could be incorporated in a more chemically accessible, suitably sized and more bioinert structure it would be a distinct advantage. In the present invention it is disclosed a group of materials where this is achieved.

There are a number of nanoparticle based contrast agents known in the art. Some of them, based on iron oxide, were used as liver specific contrast agents but are no longer on the market because of low sales volumes. A huge literature regarding experimental use of those particles is available. (e.g. Bulte, J. W. M. and Modo, M. M. J. Eds. "Nanoparticles in Biomedical Imaging" Springer, 2008). Although the present invention deals with nanosized structures they are not of the core-shell type that is usually implied by the term but rather based on a highly crosslinked polymer.

There is a huge literature about polymeric materials carrying chelating groups and paramagnetic metal ions for use in MRI. In general, a robust increase in relaxivity is achieved, although not as high as described in the current invention. To the best of our knowledge, none of said literature discloses polymeric frameworks carrying the bisphosphonates of the current invention.

The following literature examples are examples of relevant background publications, which in no way are to be construed as being within the scope of the current invention.

In Rongved P. *Carbohydr Res* 214, 315 (1991) is described a series of polymeric materials with a carbohydrate backbone and chelating groups attached. The materials closest to the current invention is Gadolinium(III)-dextran phosphate, which has a relaxivity of 16/mMGd/s at 20 MHz. Substantially lower than for the materials disclosed in the current invention. This material is of unknown stability. The phosphorus is incorporated in phosphate groups bound as phosphate esters as opposed to the phosphonates of the current invention. The material is thus outside the scope of the current invention.

Rongved also discloses a manganese(II)-EDTA-sucrose-epichlorohydrin conjugate with a relaxivity of 19.2/mMMn/s and a manganese(II)-EDTA-aminoethyldextran conjugate with a relaxivity of 12.8/mMMn/s. Both values are substantially lower than those of the materials of the current invention, especially since they were measured at the low frequency of 20 MHz. The materials fall outside the scope of the current invention.

In WO2010135167 is described a polystyrene based bisphosphonate material. There is no attempt to produce nanostructures but rather bulk materials.

The literature describing the use of dendrimers with specific chemical structure (as opposed to the polymer based structures of the current invention) and molecular weight is very large.

The most well known example of a dendrimer used as an MR contrast agent is Gadomer 17 (Turetschek, K. et al. *J. Magn. Reson. Imaging* 20, 138 (2004)) which, however, never reached clinical practice. This approach to nanosized structures suffers from very costly chemical synthesis. In part because of the many chemical steps and in part from the difficulty of purification and identification of the many possible impurities. Also, relaxivities as high as those found by the inventors of the current invention has, to our knowledge, never been reported in this field.

The rationale behind the good results of using macromolecular agents as MRI contrast agents with high sensitivity and selectivity for tumor diagnosis is the Enhanced Permeation and Retention (EPR) effect, also called passive tumor targeting. It is based on the fact that the capillaries of healthy tissues are virtually impermeable to molecules larger than 3-4 nm whereas the capillaries of fast growing tumor tissue are much leakier. Although in no way certain or limiting, it is conceivable that the EPR effect is the basis of the favorable tumor imaging properties of the current invention.

There are a number of phosphonate containing monomeric chelates of gadolinium known in the art while manganese-phosphorus combinations are less common but not unknown (Pan, D. et al. *WIREs Nanomed Nanobiotechnol* 3, 162, 2011). They are not in any way remarkable in their MRI properties and reported relaxivities are moderate. An example of one carrying a bisphosphonate is found in Vitha, T. et al. *Dalton Transactions p* 3204 (2009).

SUMMARY OF THE INVENTION

The first aspect of the present disclosure relates to nanostructures comprising nanosized structures based on a polymeric framework or scaffolding comprising or adorned with at least five geminal bisphosphonate groups —P=O($OR^1$)($OR^2$)— which in the context of the present invention is equal to —$R^4R^3C(P=O(OR^1)(OR^2))_2$— wherein $R^1$ and $R^2$ are independently selected from a negative charge, H, alkyl and aryl.

The second aspect of the present disclosure relates to nanostructures comprising paramagnetic manganese ions, incorporated in nanosized structures based on a polymeric framework or scaffolding comprising or adorned with at least five geminal bisphosphonate groups —P=O($OR^1$)($OR^2$)— which in the context of the present invention is equal to —$R^4R^3C(P=O(OR^1)(OR^2))_2$, as mentioned above— wherein $R^1$ and $R^2$ are independently selected from a negative charge, H, alkyl and aryl.

Although the term "nanosized" is generally construed to cover anything smaller than 100 nm the focus of the current invention is entities of highly branched or crosslinked structures of a roughly globular shape and an average size (hydrodynamic diameter) of 1-100 nm, or in some embodiments 2-50 nm, 3-10 nm or 3-7 nm.

The second aspect of the present disclosure relates to methods for producing such nanostructures, both those comprising manganese ions and those not comprising such ions.

The third aspect of the present disclosure relates to compositions, such as pharmaceutical compositions, comprising such nanostructures, in particular those nanostructures that comprise paramagnetic manganese ions, and also to the use of such nanostructures, in particular those that comprise paramagnetic manganese ions, as contrast agents of clinical utility, in particular use as contrast agents for MRI.

Some advantages with the nanostructures disclosed herein over prior art are the combination of a relaxivity of an order of magnitude higher than the materials currently on the market, combined with a size suitable for selective accumulation in tumor tissue and a good biotolerability. This renders the nanostructures of the current invention, in particular those nanostructures that comprise paramagnetic manganese ions, suitable for use as a contrast agent for MRI and in particular for tumor imaging.

Furthermore, the use of manganese instead of gadolinium as the paramagnetic component circumvents the toxicity issues connected with gadolinium.

The use of abundant manganese instead of the relatively rare gadolinium also has cost advantages in the production of the material.

SPECIFIC EMBODIMENTS

1. A nanostructure comprising manganese ions incorporated in a polymeric framework comprising at least five geminal bisphosphonate groups, wherein the geminal bisphosphonate groups independently of each other are incorporated as

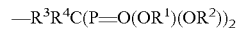
—$R^3R^4C(P=O(OR^1)(OR^2))_2$ (which is equal to —$R^4R^3C(P=O(OR^1)(OR^2))_2$) wherein $R^1$ and $R^2$ are independently selected from the group consisting of a negative charge, H, alkyl and aryl, and wherein at least one of $R^3$ and $R^4$ is a group connected to the polymeric framework with the proviso that when only one of $R^3$ and $R^4$ is such a connected group, the other of $R^3$ and $R^4$ is either a group being able to connect to the polymeric framework, or the residue of such a group, or selected from the group consisting of H, OH, $OR^5$ and $R^5$, wherein $R^5$ is a lower alkyl.

2. A nanostructure according to embodiment 1, wherein the manganese ions are manganese (II) ions.

3. A nanostructure according to embodiment 1 or 2, wherein $R^1$ and $R^2$ are independently selected from the group consisting of a negative charge, H, alkyl and methyl.

4. A nanostructure according to any one of the embodiments 1-3, wherein the group connected to the polymeric framework, and/or the group being able to connect to the polymeric framework or the residue of such a group is selected from the group consisting of:

($CH_2$)$_n$Si($R^x$)$_3$ wherein $R^x$ independently is a lower alkyl, OH, $O^-$, or O—, wherein — denotes a bond to the polymeric framework, and wherein n is 1-5, ($CH_2$)$_n$COR$^y$ wherein $R^y$ is O—, $NH_2$, $NHR^z$, $NR^z_2$, or a bond to the polymeric framework, wherein $R^z$ is a lower alkyl and wherein n is 1-5 and — denotes a bond to the polymeric framework, and ($CH_2$)$_n$SO$_2R^y$ wherein $R^y$, is O—, $NH_2$, $NHR^z$, $NR^z_2$, or a bond to the polymeric framework, $R^z$ is a lower alkyl and n is 1-5 and — denotes a bond to the polymeric framework.

5. A nanostructure according to any one of the embodiments 1-4, which comprises silicon atoms.

6. A nanostructure according to any one of the embodiments 1-5, wherein $R^3$ and/or $R^4$ are/is selected from the group consisting of —($CH_2$)$_n$—Si($R^x$)$_3$, wherein $R^x$ independently is a lower alkyl, OH, $O^-$, or O—, wherein — denotes a bond to the polymeric framework, and wherein n is 1-5.

7. A nanostructure according to any one of the embodiments 1-6, wherein the hydrodynamic diameter of the nanostructure is 2-50 nm.

8. A nanostructure according to any one of the embodiments 1-7, wherein the hydrodynamic diameter of the nanostructure is 3-10 nm.

9. A nanostructure according to any one of the embodiments 1-8, wherein the hydrodynamic diameter of the nanostructure is 3-7 nm.

10. A nanostructure according to any one of the embodiments 1-7, wherein the hydrodynamic diameter of the nanostructure is 10-50 nm.

11. A nanostructure according to any one of the embodiments 1-7 or 10, wherein the hydrodynamic diameter of the nanostructure is 10-20 nm.

12. A nanostructure according to any one of the embodiments 1-11, wherein the polymeric framework comprises monomer residues containing a geminal bisphosphonate group and two organo-oxysilane groups.

13. A nanostructure according to any one of the embodiments 1-11, wherein the polymeric framework is derived from polyethyleneimine.

14. A nanostructure according to embodiment 13, wherein the P/N molar ratio is 0.1-3.

15. A nanostructure according to any one of the embodiments 1-14, wherein the P/Mn molar ratio is 7-20.

16. A nanostructure according to any one of the embodiments 5 or 6-12 or 14-15 when dependent on embodiment 5, wherein the Si/Mn molar ratio is 5-20.

17. A nanostructure according to any one of the embodiments 5 or 6-16 when dependent on embodiment 5, wherein the Si/P molar ratio is 0.7-1.3.

18. A nanostructure according to any one of the claims 1-17 wherein the manganese ions are coordinated to the phosphonate groups.

19. A nanostructure according to any one of the embodiments 1-18, wherein said nanostructure further comprises hydrophilic groups attached to the outer parts.

20. A nanostructure according to embodiment 19, wherein the hydrophilic groups comprise —$(CH_2CH_2O)_nCH_3$ moieties wherein n=4-50.

21. A nanostructure according to any one of the embodiments 1-20, wherein the polymeric framework comprises monomer residues of the generic structure

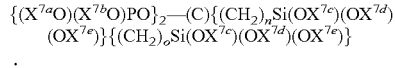

wherein
$X^{7a}$, $X^{7b}$, $X^{7c}$, $X^{7d}$, $X^{7e}$ are independently selected from H, $C_{1-8}$ alkyl and benzyl;
and
n and o are independently selected from 1-5.

22. A composition comprising a nanostructure according to any one of the embodiments 1-21.

23. A pharmaceutical composition comprising a nanostructure according to any one of the embodiments 1-21.

24. Use of a nanoparticle according to any one of the embodiments 1-21 or composition according to embodiment 22 or 23, as a MRI contrast agent.

25. A method for obtaining nanostructure according to any one of the embodiments 1-21, comprising:
obtaining nanostructures of a polymeric framework comprising geminal bisphosphonates and
contacting said nanostructures with manganese ions.

26. A method according to embodiment 25, further comprising a step wherein the nanostructures are purified by ultrafilatration.

27. A method for obtaining a nanostructure according to any one of the embodiments 13 or 14-21 when dependent on embodiment 13, wherein a gemina) bisphosphonate is grafted to a polymeric framework derived from polyethyleneimine which subsequently is loaded with manganese ions.

28. A method for obtaining a nanoparticle according to any one of the embodiments 12 or 13-21 when dependent on embodiment 12, wherein said silanes are provided in a solvent mixture containing water and one or more other solvent(s) that are miscible with water.

29. A product obtainable by a method according to any one of the embodiments 25-28.

30. A nanostructure comprising a polymeric framework comprising at least five geminal bisphosphonate groups, wherein the geminal bisphosphonate groups independently of each other are incorporated as

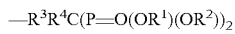

(which is equal to —$R^4R^3C(P=O(OR^1)(OR^2))_2$)
wherein $R^1$ and $R^2$ are independently selected from the group consisting of a negative charge, H, alkyl and aryl, and wherein at least one of $R^3$ and $R^4$ is a group connected to the polymeric framework with the proviso that when only one of $R^3$ and $R^4$ is such a connected group, the other of $R^3$ and $R^4$ is either a group being able to connect to the polymeric framework, or the residue of such a group, or selected from the group consisting of H, OH, $OR^5$ and $R^5$, wherein $R^5$ is a lower alkyl.

31. A nanostructure according to embodiment 30, wherein $R^1$ and $R^2$ are independently selected from the group consisting of a negative charge, H, alkyl and methyl.

32. A nanostructure according to embodiment 30 or 31, wherein the group connected to the polymeric framework, and/or the group being able to connect to the polymeric framework or the residue of such a group is selected from the group consisting of:
$(CH_2)_n Si(R^x)_3$ wherein $R^x$ independently is a lower alkyl, OH, O⁻, or O—, wherein — denotes a bond to the polymeric framework, and wherein n is 1-5,
$(CH_2)_n COR^y$ wherein $R^y$ is O—, $NH_2$, $NHR^z$, $NR^z_2$, or a bond to the polymeric framework, $R^z$ is a lower alkyl and n is 1-5, and — denotes a bond to the polymeric framework, and
$(CH_2)_n SO_2R^y$ wherein $R^y$ is O—, $NH_2$, $NHR^z$, $NR^z_2$, or a bond to the polymeric framework, $R^z$ is a lower alkyl and n is 1-5 and — denotes a bond to the polymeric framework.

33. A nanostructure according to any one of the embodiments 30-32, which comprises silicon atoms.

34. A nanostructure according to any one of the embodiments 30-33, wherein $R^3$ and/or $R^4$ are/is selected from the group consisting of —$(CH_2)_n$—$Si(R^x)_3$, wherein $R^x$ independently is a lower alkyl, OH, O⁻, or O—, wherein — denotes a bond to the polymeric framework, and wherein n is 1-5.

35. A nanostructure according to any one of the embodiments 30-34, wherein the hydrodynamic diameter of the nanostructure is 2-50 nm.

36. A nanostructure according to any one of the embodiments 30-35, wherein the hydrodynamic diameter of the nanostructure is 3-10 nm.

37. A nanostructure according to any one of the embodiments 30-36, wherein the hydrodynamic diameter of the nanostructure is 3-7 nm.

38. A nanostructure according to any one of the embodiments 30-35, wherein the hydrodynamic diameter of the nanostructure is 10-50 nm.

39. A nanostructure according to any one of the embodiments 30-35 or 38, wherein the hydrodynamic diameter of the nanostructure is 10-20 nm.

40. A nanostructure according to any one of the embodiments 30-39, wherein the polymeric framework comprises monomer residues containing a geminal bisphosphonate group and two organo-oxysilane groups.

41. A nanostructure according to any one of the embodiments 30-40, wherein the polymeric framework is derived from polyethyleneimine.

42. A nanostructure according to embodiment 41, wherein the P/N molar ratio is 0.1-3.

43. A nanostructure according to any one of the embodiments 33 or 34-42 when dependent on embodiment 33, wherein the Si/P molar ratio is 0.7-1.3.

44. A nanostructure according to any one of the embodiments 30-43, wherein said nanostructure further comprises hydrophilic groups attached to the outer parts.

45. A nanostructure according to embodiment 44, wherein the hydrophilic groups comprise —$(CH_2CH_2O)_n CH_3$ moieties wherein n=4-50.

46. A nanostructure according to any one of the embodiments 30-45, wherein the polymeric framework comprises monomer residues of the generic structure

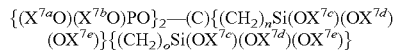

wherein
$X^{7a}$, $X^{7b}$, $X^{7c}$, $X^{7d}$, $X^{7e}$ are independently selected from H, $C_{1-8}$ alkyl and benzyl; and
n and o are independently selected from 1-5.

DEFINITIONS OF TERMS

The term "nanostructure" as used herein related to an entity with a total diameter from 1-100 nm of essentially globular shape, i.e. excluding flakes, rods, tubes and ribbons. As used herein the term excludes the structures often referred to as "core-shell nanoparticles" or just "nanoparticles" which have a mineral or metal core and an organic coating.

The term "polymeric framework" as used herein relates to a covalently bound group of atoms forming either a multi-branched tree like structure or a network structure with multiple crosslinks. Polymeric frameworks are formed from the linking of monomers and/or oligomers and/or crosslinkers via covalent bonds. Typical monomers can be found in textbooks of polymer chemistry such as J. R. Fried, "*Polymer Science and Technology*" Prentice Hall 1995. Some examples of monomers are styrene, propylene, ethylene, tetrafluoroethylene, trifluoroethylene, difluoroethylene, methyl acrylate, ethyl acrylate, hydroxyethyl acrylate, acrylamide, methyl methacrylate, ethyl methacrylate, hydroxyethyl methacrylate, $H_2N$—$(CH_2)_n$—COOH, where n is 1-10, 3-aminobenzoic acid, 4-aminobenzoic acid, N-vinyl pyrolidone and silicone precursors like $(CH_3COO)_2Si(CH_3)_2$. Some examples of polymers are polymers formed from matching pairs of monomers like terephtalic acid+1,4 diamino benzene, terephtalic acid+ethylene glycol, and HCOO—$(CH_2)_n$COOH+ $H_2N$—$(CH_2)_m$—$NH_2$, where n and m independently are 1-10. Oligomers with 2-10 monomer units linked can be used as precursors. Some examples of oligomers different from linked groups of the above monomers are cyclic or polycyclic silanes such as hexamethylcyclotrisiloxane, 2,4,6,8-Tetramethylcyclotetrasiloxane, and decamethylcyclopentasiloxane. Typical crosslinkers can be found in textbooks of polymer chemistry such as J. R. Fried, "*Polymer Science and Technology*" Prentice Hall 1995. Some examples of crosslinkers are N,N'-methylenebis(acrylamide), epichlorohydrin, divinylbenzene, 1,3-divinyltetramethyldisiloxane, 1,3-phenylenediisocyanate, 3,3'-biphenyltetracarboxylic acid dianhydride, 1,4-butanedioldivinylether, tetraethoxysilane, oligosilicates such as meta silicate, or silsequioxanes, organosilanes such as bis(triethoxysilyl)methane, bis(triethoxysilyl)ethane, bis(triethoxysilyl)propane, bis(triethoxysilyl)butane, methyl triethoxysilane, ethyl triethoxysilane, and propyl triethoxysilane.

This polymeric framework constitutes the skeleton of the nanostructure. The skilled person realizes that the random nature of the polymerization process causes the materials to be mixtures of many similar but not identical branching patterns, crosslink position and molecular weight.

The term "geminal bisphosphonate group" refers to two phosphonate groups separated by one carbon atom, i.e. the phosphonate groups are bound to the same carbon. Compounds comprising such a geminal bisphosphonate group are often referred to as 1,1-bisphosphonates (or 1,1-diphosphonates). The phosphonate groups in the geminal bisphosphonate group may be substituted. In some embodiments phosphonate groups each have the formula —P=O($OR^1$)($OR^2$) wherein $R^1$ and $R^2$ are independently selected from the group consisting of a negative charge, H, alkyl and aryl.

The term "group connected to the polymeric framework" refers to a chemical group where a covalent bond formally substituting a hydrogen atom of the polymeric framework. Chemical groups encompassed by this definition are generally short linear residues of hydrocarbons, ethers, amides or esters. Some typical examples are —$(CH_2)_n$—, —$(CH_2)_n$CO—, —$(CH_2)_n$COCl—, —$(CH_2)_n$CONH—, and —$(CH_2)_n$Si(O—)$_3$. In this context the word "short" means that n is 1-8.

The term "group forming part of the polymeric framework" refers to a situation where the two phosphonate groups are sitting on the same carbon atom of the polymeric framework.

The term "group being able to connect to the polymeric framework" refers to precursors of the above groups referred to as connected to the polymeric framework. Some examples are —$(CH_2)_n$OH, —$(CH_2)_n$Br, —$(CH_2)_n$COCl—, —$(CH_2)_n$COCH$_3$, —$(CH_2)_n$COCH$_2$CH$_3$, —$(CH_2)_n$COO—, —$(CH_2)_n$CONH$_2$, and $(CH_2)_n$Si(OEt)$_3$.

The term "bio-inert" as used herein refers to a material that is biocompatible, i.e. harmless to a living organism and at the same time stable to degradation in vivo.

The term "DLS" as used herein is an acronym for dynamic light scattering, a particle sizing method, and may also be referred to as Photon Correlation Spectroscopy or Quasi-Elastic Light Scattering. The DLS sizes given as stated in the text and in the claims, if nothing else is specified, refers to the position of the maximum of the volume average peak for a sample measured at 25° C. in neutral aqueous solution with an ionic strength corresponding to 150 mM NaCl.

The term "globular" as used herein is meant to describe nanostructures with a shape such that the minor axis is no more than half of the major axis, i.e. the longest axis through the center (point of weight) of the structure is no more than twice the length of the shortest axis through the same point.

The term "hydrophilic organic residue" as used herein refers to an organic residue that promote solubility in aqueous solvents and in the current invention it is implicit that they are bio-inert, which excludes polypeptides and complex carbohydrates. Examples of suitable hydrophilic organic residues are any group containing carbon with a molecular composition (aO+bN)/(cC+dS+eSi+fP)>0.3 where a, b, c, d, e and f are the mol percentage of oxygen (O), nitrogen (N), carbon (C), sulfur (S), silicon (Si) and phosphorus (P), respectively.

The term "activated silane" as used herein refers to a silane of the following type $R_nSi(X)_{4-n}$, where X is an alkoxy group, aryloxy group, a halogen, a dialkylamino group, a nitrogen containing heterocycle or an acyloxy group.

The term "oxysilane" as used herein refers to any organic compounds with one or more oxygen atoms attached to the silicon atom. Non-limiting examples thereof are:

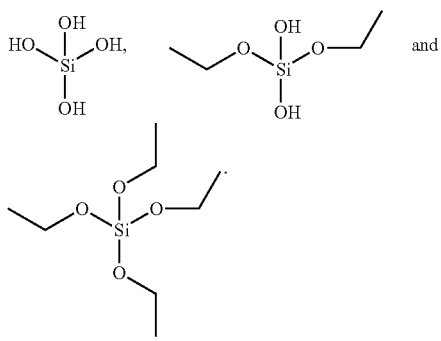

The term "organosilane" as used herein refers to organic compounds containing one or more carbonsiliconbonds.

The term "organo-oxysilane" as used herein refers to organic compounds containing one or more carbon atoms and one or more oxygen atoms attached to the silicon atom. Non-limiting examples thereof are:

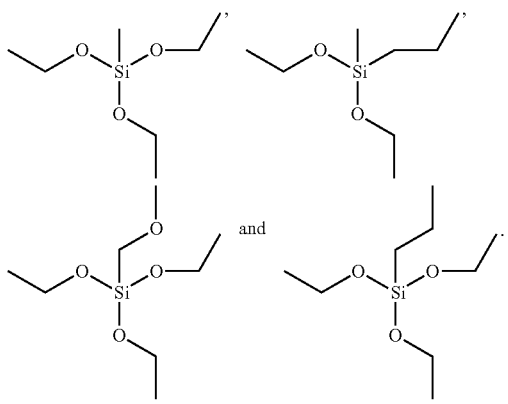

The terms "hydrocarbon" and "hydrocarbon chain" are used herein to denote an organic residue consisting of hydrogen and carbon. The hydrocarbon may be fully saturated or it may comprise one or more unsaturations. The hydrocarbon may contain any number of carbon atoms between 1 and 50.

The term "alkyl" as used herein refers to a straight or branched hydrocarbon chain fully saturated (no double or triple bonds) hydrocarbon group. The alkyl group may in the present text have 1 to 15 carbon atoms. The alkyl group of the compounds may be designated as "$C_{1-15}$ alkyl" or similar designations. Typical alkyl groups include, but are in no way limited to, methyl, ethyl, propyl, isopropyl, butyl, isobutyl, tertiary butyl, pentyl, hexyl and the like.

The term "lower alkyl" as used herein refers to an alkyl having 1-8 carbon atoms.

The term "lower alcohol" as used herein refers to an alcohol having 1-8 carbon atoms.

Whenever it is used herein, unless otherwise stated, a numerical range such as "1 to 8" or "1-8" refer to each integer in the given range; e.g., "1 to 8 carbon atoms" means that the alkyl group may consist of 1 carbon atom, 2 carbon atoms, 3 carbon atoms, etc., up to and including 8 carbon atoms. There are, however some exceptions which are clear to the skilled persons. In particular, whenever a range is given herein for a molar ratio, such as the P/N molar ratio or the Si/P molar ratio in the nanostructures, for a diameter or size, for a pH, for a period of time, for a concentration, for an osmolality or for a temperature, the range includes also all decimal numbers falling within the range.

As used herein, the term "alkoxy" refers to the formula —OR wherein R is a $C_{1-8}$ alkyl, e.g. methoxy, ethoxy, n-propoxy, 1-methylethoxy (isopropoxy), n-butoxy, iso-butoxy, sec-butoxy, tert-butoxy, amyloxy, iso-amyloxy and the like. An alkoxy may be optionally substituted.

As used herein the term "aryloxy" refers to RO— in which R is an aryl wherein, "aryl" refers to a carbocyclic (all carbon) ring or two or more fused rings (rings that share two adjacent carbon atoms) that have a fully delocalized pi-electron system. The aryl ring may be a 4-20 membered ring. Examples of aryl groups include, but are not limited to, benzene, naphthalene and azulene. An aryl group may be optionally substituted, e.g., phenoxy, naphthalenyloxy, azulenyloxy, anthracenyloxy, naphthalenylthio, phenylthio and the like. An aryloxy may be optionally substituted As used herein the term "acyl" refers to a carbonyl group, i.e. —C(=O)—.

As used herein the term "acyloxy" refers to an oxygen atom connected via a carbonyl group, i.e. —C(=O)—O—.

As used herein the term "heterocycle" refers to a stable 3-18 membered ring which consists of carbon atoms and from one to five heteroatoms selected from the group consisting of nitrogen, oxygen and sulfur. The heterocycle may be monocyclic, bicyclic or tricyclic.

The term "strong base" as used herein refers in the current context to bases that are stronger than hydroxide and not compatible with aqueous environments.

The term "hydrodynamic diameter" as used herein refers to the diameter of the hypothetical hard sphere that diffuses at the same speed as the particle. Hydration and shape is included in the behavior of the sphere. The term is also known as "Stokes diameter" or "Stokes-Einstein diameter."

The term "conjugate" as used herein refers to a molecular entity that is a fluorescence marker, dye, spin-label, radioactive marker, ligand to a biological receptor, chelate, enzyme inhibitor, enzyme substrate, antibody or antibody related structure. See e.g. "Bioconjugate Techniques", Greg T. Hermanson second edition, Elsevier 2008, ISBN 978-0-12-370501-3 for background on the subject.

The terms "handle for conjugation" and "attachment point" both refer to a bifunctional molecule that can bind to, or be incorporated in, the polymer network but leaving one reactive group that can be linked to a conjugate, as defined above. A typical, but not exclusive, example would be $(EtO)_3SiCH_2CH_2CH_2NH_2$.

The acronym TEOS stands for tetraethoxysilane.
The acronym DCM stands for dichloromethane.
The abbreviation "bisbis" stands for 1,1-bis(triethoxysilyl-propyl)-1,1-bis(dimethylphosphonato)methane, the product of example 1b.

DETAILED DESCRIPTION OF THE INVENTION

In a first aspect, the present invention deals with paramagnetic manganese ions incorporated in nanosized structures (nanostructures) based on a polymeric framework or scaffolding comprising or adorned with a multitude of phosphonate groups —P=O(OR$^1$)(OR$^2$) where R$^1$ and R$^2$ are independently selected from a negative charge, H, alkyl or aryl.

When at least one of $R^1$ or $R^2$ is H the resulting phosphonic acid is ionized to a pH dependent extent.

As mentioned above, the term "nanostructure" relates to a structure with a total diameter of 1-100 nm.

In some embodiments of the invention Wand $R^2$ are independently selected from the group consisting of a negative charge, H and methyl.

To the carbon atom separating the bisphosphonate groups, i.e. the intervening carbon atom, one or more bonds to the polymeric framework is/are present. Thus, the intervening carbon atom may be either part of, or attached to, the polymeric framework. Of particular interest are the structures of the type $(R^3R^4C(P=O(OR^1)(OR^2))_2$ where $R^1$ and $R^2$ are independently selected from H or alkyl or aryl and at least one of $R^3$ and $R^4$ is a group capable of being connected to the polymeric framework of the material. In the case where only one of $R^3$ and $R^4$ is such a group, the remaining group is selected from the group consisting of H, OH, $OR^5$ (with $R^5$ being lower alkyl), and lower alkyls.

In some embodiments of the present invention $R^3$ and/or $R^4$ are/is selected from the group consisting of $—(CH_2)_n—Si(R^x)_3$, wherein $R^x$ independently is a lower alkyl, OH, $O^-$, or O—, wherein — denotes a bond to the polymeric framework, and wherein n is 1-5.

In some embodiments of the present invention $R^3$ is $—(CH_2)_nCO—$ (with the carbonyl group forming the bond to the polymeric framework) and $R^4$ is H and n=1-5. In some of these embodiments n=1.

In some embodiments of the present invention $R_3$ and $R_4$ are independently $—(CH_2)_n—SiO_3$, where n=1-5 and the silane is part of the polymeric framework by the formation of Si—O—Si bonds as expanded upon later in the text.

In some embodiments of the present invention $R_3$ and $R_4$ are both $—(CH_2)_n—SiO_3$, wherein n=3 and the silane is part of said polymeric framework in the above manner.

It is also conceivable to use phosphonic amides, chlorides or fluorides instead of phosphonic esters or acids as components or starting materials of the compounds described here. The phosphonates may be present in their free form or as esters or as amides or any mixture thereof.

In some embodiments of the invention the phosphonates is a mixture of free phosphonates and the methyl esters of said phosphonate.

The polymeric framework, to which said phosphonate groups are linked, can be constructed from a large number of well known monomers as can be found in any book on polymer chemistry (e.g. J. R. Fried, "*Polymer Science and Technology*" Prentice Hall 1995). Some non-limiting examples are polyacrylates, polymethacrylates, polyamides, polystyrene, polydimethylsiloxanes (silicones), polyorganosilanes, polyamines such as polyethyleneimine, or carbohydrates; especially highly branched or crosslinked structures.

The nanostructures according to the present disclosure are, as mentioned above, structures with a roughly globular shape and an average size (hydrodynamic diameter) of 1-100 nm; in some embodiments the average size may be 2-50 nm, in other embodiments the average size may be 3-10 nm, or 3-7 nm, or 10-50 nm, or 10-20 nm.

In some embodiments of the invention, a non-limiting example being use as an intravenous contrast agent, the average hydrodynamic diameter of the nanostructures is 3-7 nm.

In some embodiments, for example embodiments where the material is used for lymph node imaging, of the invention the average hydrodynamic diameter of the nanostructures is 10-50 nm or 10-20 nm.

The hydrodynamic diameter referred to, is the diameter of the equivalent hard sphere as calculated from the diffusion coefficient, according to the Stokes-Einstein equation. The diffusion coefficient is in turn calculated from the time dependent light scattering data obtained by the Dynamic Light Scattering (DLS) technique. As a comparison, bovine serum albumin is measured to have a hydrodynamic diameter of 6.5 nm by DLS in aqueous solution, very much in agreement with the crystal structure. Depending on whether the number average, volume average, or scattered intensity average is used, the values may be somewhat different. The volume average is generally the most useful since it shows which particle size the bulk of the material has. The average diameters referred to in this text refers to volume averages.

It is favorable to use structures with a branched or network like structure to form the globular structures desired in the current invention. One established way of achieving a network structure is by introducing cross-links via the incorporation of a fraction of bifunctional monomers in the polymerization process. A well known example is the crosslinking of polystyrene with divinylbenzene.

Branching structures can be formed by having more than one reactive position in the monomers ("*The architecture and surface behavior of highly branched molecules*" Peleshanko, S., Tsukruk, V. V., *Prog. Polym. Sci.* 33, 523 (2008)). A well-known example is the formation of the highly branched polyethyleneimine by the polymerization of aziridine. Polyethyleneimine contains a mixture of primary, secondary and tertiary amino groups and it has a branching random structure as indicated in the scheme below. The exact structure is only to be construed as typical and in no way limiting to the current invention. The bisphosphonates crucial to the current invention may be attached to the primary and/or secondary amino groups.

In some embodiments of the invention the polymeric framework is polyethyleneimine. Below a typical polyethyleneimine structural fragment is shown. The dashed bonds indicate that the polymeric network continues.

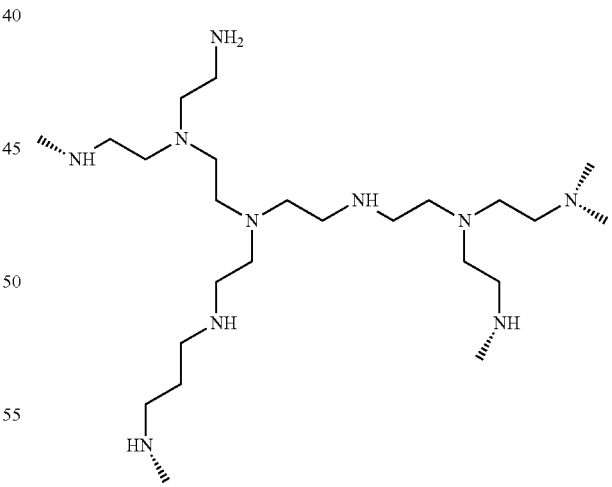

When incorporating the bisphosphonate in a polyacrylate framework it is conceivable to attach the bisphosphonate to the amide nitrogen through a short linker. A typical but non limiting example of a structural fragment from such a material would be the structure below with $R^1$ and $R^2$ as defined earlier in the text, n from 1-5 and the dashed bonds indicating that the fragment belongs to a polymer. It is also conceivable to attach the bisphosphonate directly to the carbon skeleton.

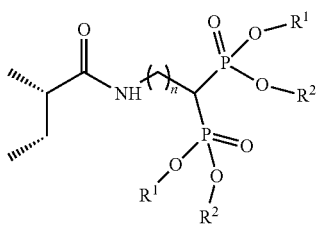

Frameworks based on polyaromatics like polystyrene or polyvinylpyridine can also be envisioned. The bisphosphonate is then attached to the aromatic system. Polyamides like polyvinylpyrrolidinone are also conceivable.

A suitable degree of cross linking is required to form the globular nanostructures of the current invention. Incorporation of 1-100% of a di-, tri- or tetrafunctional cross-linking agent is preferred. A non-limiting list of typical cross-linking agents are N,N'-methylenebis(acrylamide), epichlorohydrin, divinylbenzene, 1,3-divinyltetramethyldisiloxane, 1,3-phenylenediisocyanate, 3,3'-biphenyltetracarboxylic acid dianhydride, 1,4-butanedioldivinylether, tetraethoxysilane, oligosilicates such as meta silicate, or silsequioxanes, organosilanes such as bis(triethoxysilyl)methane, bis(triethoxysilyl)ethane, bis(triethoxysilyl)propane, bis(triethoxysilyl)butane, methyltriethoxysilane, ethyl triethoxysilane, and propyl triethoxysilane.

The degree of polymerization is adjusted to yield products of the desired size by manipulating the process parameters as known in the art. The desired size can not only be expressed as hydrodynamic diameter but also as the degree of polymerization (average number of monomers). It is less useful than the hydrodynamic diameter but it is another way of conceptualizing the structures and included not as limiting but rather as reference. For example, for a polymer with a density close to 1 g/ml the preferred sizes range from 25-3 000 000 or 25-375 000 or 80-3000 or 80-1000 monomers.

It is conceivable to mix all of the said polymer frameworks in any chemically compatible combination, either by mixing the monomers prior to polymerization, or by grafting a second polymer to a first polymer.

One particularly advantageous framework is formed by the condensation polymerization of trialkoxyorganosilanes $R^5$—Si$(OR^6)_3$, with $R^5$ being H or an organic residue and $R^6$ independently being a lower alkyl or aryl. Such a framework has the property of being highly polar, hence compatible with water, and the degree of crosslinking can be controlled by the process parameters during production. It is advantageous to use monomers with more than one trialkoxysilyl group present.

In some embodiments of the invention there are two alkoxysilane groups present in the monomer.

In some embodiments of the invention said alkoxysilanes are separated by 1-10 carbon atoms or 3-9 carbon atoms.

In some embodiments of the invention said alkoxysilanes are separated by 7 carbon atoms.

In some embodiments of the invention said alkoxysilanes are separated by three or five carbon atoms.

In some embodiments of the invention the two phosphonate groups are part of the group $R^5$.

In some embodiments of the invention said two silanes are separated by 7 carbon atoms and the two phosphonate groups are part of the group $R^5$.

In some embodiments of the invention said silanes have the generic structure:

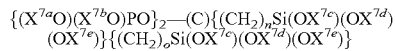

wherein
$X^{7a}$, $X^{7b}$, $X^{7c}$, $X^{7d}$, $X^{7e}$ are independently selected from H, $C_{1-8}$ alkyl and benzyl;
and
n, and o are independently selected from 1-5.

In some embodiments a second silane such as a disilane is grafted onto the polymeric framework formed by the first disilane The reactivity of the trialkoxy silanes towards polymerization varies with the identity of the $R^6$ groups. We have found this to be a critical factor in the control of molecular size during production and found the methyl and ethyl, in particular the latter, to be suitable for yielding the structures of the present invention although it is conceivable to use any other lower alkyl group, aryl, silyl amide, acyl, silylfluoride or silylchloride.

In some embodiments of the invention $R^6$ is an ethyl group.

There are many different ways trialkoxy silanes may link up via Si—O—Si bonds. Dimeric structural elements as well as linear, branched, and cyclic are known (R. J. Fessenden, J. S. Fessenden, "*Trends in Organosilicon Biological Research*" in *Advances in Organometallic Chemistry* vol. 18 p. 275). Also Silicon-oxygen cage structures of various sizes are well known from the literature (Hanssen, R. J. M. et al. *Eur. J. Inorg. Chem* 675 (2004)) and residual alkoxy groups or free silanol groups may also be present to different degrees. It is also conceivable that the paramagnetic metal ions crucial to the current invention to some extent are coordinated by Si—O— groups. Some structural elements, though in no way to be construed as limiting, that may be present in such structures are shown in scheme 1.

Scheme 1: Illustration of some Si—O—Si structures that may be used in the present invention; R is any organic residue

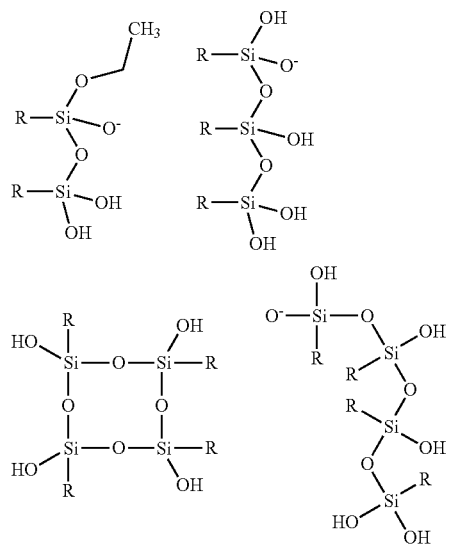

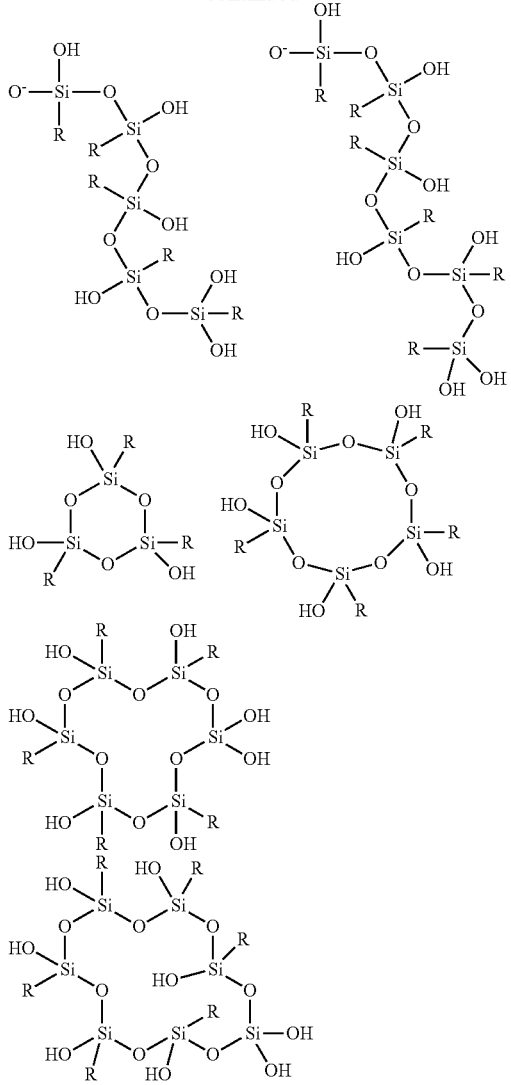

The geminal bisphosphonate structure $R^3R^4C(P=O(OR^1)(OR^2))_2$ which is at the core of the present invention is well known to bind multivalent cations like calcium strongly. An advantage of the materials of the current invention is that they show a preference of manganese over calcium and magnesium at physiological concentrations (this is further illustrated below in Example 15).

The phosphonate groups may be completely present in their ester form, completely or partially hydrolyzed to their acid form and subsequently ionized to some extent from partial to complete according to the pH value of the surrounding medium or any mixture thereof. It is optimal to load the manganese ions into the polymer at a neutral or basic pH. Anywhere from pH 12-6 or pH 11-8 or preferably 10.5 to 9.5 is useful. This indicates that it is, at least in part or sometimes or even completely, the anionic form of the hydrolyzed phosphonate, which plays an important part in the binding of the metal ions. Not only phosphonate esters or acids but also phosphonic amides may be contemplated as part of the material or to be used as starting material.

We have discovered that when the bisphosphonate structure is incorporated into a polymeric framework, preferably hydrophilic, and allowed to bind manganese(II), a spectacular increase in relaxivity is achieved. The manganese chelate of the monomeric bisphosphonate zoledronic acid has a relaxivity of 2.3/mM Mn/s (as shown in example 17) and manganese plus the monomeric bisphosphonate methylenediphosphonic acid has a relaxivity of 1/mM Mn/s. The relaxivities of the polymeric manganese loaded materials of the present invention range from 24-48/mM Mn/s.

Specifically, when polyethyleneimine is derivatized with an activated ester of a geminal bisphosphonate as described in example 9, and, subsequently, loaded with manganese(II) ions, a material with a relaxivity of 24/mM Mn/s is obtained. This is substantially higher than the previously mentioned relaxivity of the zoledronic acid complex, thus showing the advantage of incorporating the bisphosphonate in a polymeric framework. The phosphorous to nitrogen molar ratio in such materials can range from 0.1 to 3 and it is preferably between 0.2 and 0.8.

To further show that the relaxivity originates from the combination of geminal bisphosphonates with a polymer, the corresponding "naked" polymers were also tested. Polyethyleneimine without any additives binds manganese very poorly and the relaxivity of the little that is bound to the polymer is very low (0.8/mM/s). Also the polyorganosilane formed from $(EtO)_2P=O-CH_2-CH_2-Si(OEt)_3$ gives the rather unimpressive relaxivity of 3.0/mM Mn/s after loading with manganese. All taken together, this proves that the surprisingly high relaxivity inherent in the materials of the current invention comes from the combination of all the features of being polymeric, carrying geminal bisphosphonates and incorporating a paramagnetic metal such as manganese.

In example 22 is described how a 1,3-bisphosphonate bound to the polymeric framework of polyethyleneimine, which falls outside the scope of the current invention, has a lower relaxivity (18.5/mM/s) than the geminal bisphosphonates of the current invention ($>=24$/mM/s). It also has a poor stability in the ion exchange test we have used. It is thus reasonable to expect 1,2-bisphosphonates, as well as any 1,n-bisphosphonates where n>2 to be less desirable than the geminal bisphosphonates of the current invention.

The paramagnetic metal ions are presumably, but in no way limiting to the current invention, chelated to the phosphonate groups, and a phosphorous to manganese ratio of 10-15 seems to be the best compromise between relaxivity and stability but anywhere between 7 and 20 is conceivable. In table 1 of example 11, the effect of varying the phosphorus to manganese ratio is described in detail.

The preferred silicon to manganese ratio will then range from 5-20 and the phosphorus to silicon ratio should be around 1 such as between 0.7 and 1.3.

Optionally, a hydrophilic, bioinert material may be grafted onto the outer parts of the nanostructures of the current invention. Said outer parts are those parts of the nanostructure that are accessible to chemical reactions with derivatizing reagents. This can be advantageous for the biocompatibility of the material and many hydrophilic materials such as carbohydrates or hydrophilic artificial polymers, can be considered. Of particular interest are polyether compounds and especially polyethyleneglycol (PEG) derivatives. Although not limiting, the methoxy terminated PEG derivatives are preferred (m-PEG). They can be grafted in any chemically acceptable way to the polymer framework such as to oxygen, nitrogen or carbon atoms such as to residual phosphonic acid or silanol groups after metal chelation or alternatively directly to the metal free polymer. Suitable chain lengths of linear PEG derivatives are from 4 to 50 —$CH_2CH_2O$-units. Most desirable are mixtures comprising from 5 to 20 units and averaging around 10 or 11. The reagents which are most conveniently coupled to the nanostructures are amino terminated and can be coupled to residual phosphonate groups. Branched PEG derivatives are also of interest and especially structures like those in example 8, which are more compact and better at protecting the surface than linear PEG derivatives of similar molecular weight.

The number of bioinert polymer groups on each nanostructure entity may range from 10 to 1000 or from 10 to 100 or from 10 to 50.

In some embodiments the polymeric, manganese loaded bisphosphonate nanostructures of the current invention comprises linear m-PEG groups with a chain length of 5 to 20 monomer residues coupled to a fraction of the phosphonate groups through amide bonds.

In some embodiments the polymeric, manganese loaded bisphosphonate nanostructures of the current invention comprises branched PEG groups of structure X1 (example 8h) coupled to a fraction of the phosphonate groups through amide bonds.

It is conceivable to introduce handles for conjugation of the nanostructures of the present invention to various active molecular entities such as biomarkers or reporter entities. A non-limiting list of typical examples would be peptides, peptoids, proteins, antibodies, DNA-fragments, RNA-fragments, PNA, fragments, fluorophores, chelates, or small molecule pharmacological ligands.

The second major aspect of the current invention is a process to produce said nanostructures. In its broadest sense it first involves the formation of globular, nanosized polymer entities comprising a multitude of bisphosphonate groups followed by a step where the product of the first step is contacted with manganese(II) ions. Optionally, the two steps, although chemically distinct, may be carried out simultaneously in the same reaction vessel. The major features of the process are outlined in FIG. 1. At one or more instances of the process a size selection or purification step by ultrafiltration is incorporated.

A nanosized polymer globule comprising a multitude of bisphosphonates is obtained either via grafting (002) to an existing polymer globule (obtained by a polymerization step 001) or by polymerization of a monomer mixture comprising bisphosphonates (003). Depending on which polymeric framework is desired, many different polymerization initiators can be contemplated. For unsaturated monomers like styrenes and acrylates various radical initiators, such as benzoyl peroxide or azobisisobutyronitrile, are preferred. For the trialkoxy silane based monomers of one of the preferred embodiments of the current invention, it is possible to use spontaneous hydrolysis and condensation to effect the polymerization or to use acid or base catalysis. It has sometimes proven advantageous to use an addition of a pH stabilizing salt like a bicarbonate, in particular sodium bicarbonate, or a carboxylate like sodium acetate, sodium formate, or tetramethyl ammonium formate to the reaction mixture to optimize the yield of product in the size range from 3-10 nm.

Often a solvent is desirable for step 003 and although many different ones can be envisioned by one skilled in the art, it is desirable to avoid toxic solvents so water and lower alcohols such as propanol, butanol, ethylene glycol, or 1,3-propanediol are preferred. It is often desirable to optimize the yield and quality of the product by using mixtures of solvents.

In some embodiments of the process a mixture of 5-25% of water in a lower alcohol is used in step 003.

In some embodiments of the process a mixture of 5-25% of water in ethanol, 1- or 2-propanol, ethyleneglycol or 1,2- or 1,3-propanediol is used in step 003.

It has been found to be advantageous to use temperatures higher than room temperature for step 003, such as temperatures of 40-130° C. or 80-120° C. or 100-120° C. When lower alcohols are used it is necessary to work with closed, pressure resistant vessels to achieve the desired reaction temperature.

The duration of step 003 depends on the polymeric framework and mode of initiation and may range from seconds to days or weeks. For the trialkoxy silanes in some of the preferred embodiments of the current invention, is has proven advantageous to use times 6-200 hours, or 6-48 hours, or 12-36 hours, or approximately 24 hours in step 003.

In some embodiments of the invention the conditions of step 003 are a temperature of 105-115° C. and a duration of 20-30 hours.

In some embodiments of the invention the conditions of step 003 are a temperature of 105-115° C. and a duration of 30-60 hours.

In some embodiments of the invention the conditions of step 003 are a temperature of first 90-100° C. for 40-50 hours and then 105-115° C. for another 20-30 hours.

The concentration of monomers in step 003 depends on which polymeric framework is desired and can range from a molar concentration to solvent free conditions. However, for the trialkoxy silanes in one of the preferred embodiments of the current invention, it has proven advantageous to work 10-500 mM or 20-100 mM and in particular 40-80 mM monomer concentration.

In some embodiments of the invention the conditions of step 003 are first a temperature of 90-100° C. for 20-50 hours followed by 105-125° C. for 20-30 hours and a monomer concentration of 40-60 mM.

In step 002 which involves the grafting a bisphosphonate reagent to a polymeric framework the conditions are somewhat different. Especially are the temperature and concentration demands more relaxed. We have found that starting with a solution of polyethyleneimine in water optionally with the admixture of a cosolvent, at a temperature compatible with liquid water, such as room temperature and contacting it with a bisphosphonate capable of reacting with said polyethyleneimine, such as 3,3-bis(dimethoxyphosphoryl)-propanoic acid, in the presence of a compound capable of forming a reactive ester intermediate, such as N-hydroxysulfosuccinimide sodium salt in the presence of a coupling agent, such as N-(dimethylaminopropyl)-N'-ethyl carbodiimide at a temperature, such as room temperature for a time period of 1-48 hours, such as 20-24 hours, produce a material with bisphosphonates grafted to the polymeric framework.

A size selection step (004) is performed on the solution of nanostructure precursors (X) to remove undesirably large or small entities. Starting materials and solvent residues from the reaction mixture are also removed at this stage. Ultrafiltration is a preferred method of purification, especially when used in the form which is usually labeled laminar flow filtration or diafiltration. It is preferred to remove undesirably large nanostructures and/or aggregates by passing the solution through a filter with rather large pores, step 004a. Preferred nominal cut-off values for such filters are 300 kDa, or 100 kDa, or 50 kDa. In a step 004b the desired material is collected on a filter with smaller pore size. Preferred pore sizes for step 004b have nominal cut-off values at 50 kDa, 30 kDa, or 10 kDa.

The size selection step (004) may not be required if the starting material has a narrow size distribution.

In some embodiments of the invention a solution obtained from process step 002 or 003 is passed, first through a 100 kDa filter (step 004a) and, subsequently, collected on a 30 kDa filter (step 004b).

In some embodiments of the invention a solution obtained from process step 002 or 003 is passed first through a 300 kDa filter (step 004a) and subsequently collected on a 100 kDa filter (step 004b).

In some embodiments of the invention a solution obtained from process step 002 or 003 is passed first through a 50 kDa filter (step 004a) and subsequently collected on a 30 kDa filter (step 004b).

In some embodiments of the invention a solution obtained from process step 002 or 003 is passed first through a 100 kDa filter (step 004a) and subsequently collected on a 10 kDa filter (step 004b). It is advantageous to wash the material with several portions of water after step 004b to further remove monomers or solvent residues from step 001, 002 or 003.

Other ultrafiltration methods such as spin filters or dialysis can also be used although they are less scalable.

Particles of the desired size range may also be selected by size exclusion chromatography (also called gel filtration).

The step, 005, where said polymer is loaded with manganese (II) involves subjecting a solution of said polymer to manganese(II) ions. Said ions can be added to the reaction mixture in the form of a solid or as a solution. Soluble salts of manganese(II) like the fluoride, chloride, bromide, acetate, nitrate, or sulfate are preferred. It is conceivable to use less soluble sources of manganese, like MnO, too. Useful concentrations of manganese ions are from 0.1 mM-5 M such as 0.1-600 mM or 0.1-10 mM depending on the polymer concentration. As discussed previously, the phosphorus to manganese ratio is important. It is optimal to load the manganese ions into the polymer at a neutral or basic pH. Anywhere from pH 12-6 or pH 11-8 or preferably 10.5-9.5 is useful. The addition of the manganese should occur after such a time period that the pH has stabilized at the desired value. We have found times from 10 minutes to 24 hours such as from one half to two hours to be enough. After the loading of the nanostructures with manganese, the pH is adjusted to neutral (between 8 and 6 or between 7.7 and 7). The temperature for the loading may be anywhere from the freezing point to the boiling point of the solvent or solvent mixture in question and from room temperature to 60 degrees is preferred.

In an optional step 006 particles of the desired size range are separated from undesirably large or small species. Often this is not necessary since the nanostructures only changes marginally in size when the manganese is added. Step 006 may have several substeps 006a, 006b etc or, for a substep in no particular order, 006x.

Ultrafiltration is a preferred method of a size selection step 006x, especially when used in the form which is usually labeled laminar flow filtration or diafiltration. It is preferred to remove undesirably large nanostructures and/or aggregates by passing the solution through a filter with rather large pores, step 006a. Preferred nominal cut-off values for such filters are 300 kDa or 100 kDa or 50 kDa. In a step 006b the desired material is collected on a filter with smaller pore size. Preferred pore sizes for step 006b have nominal cut-off values at 50 kDa, 30 kDa or 10 kDa.

In some embodiments of the invention a solution obtained from process step 005 is passed, first through a 100 kDa filter (step 006a) and, subsequently, collected on a 30 kDa filter (step 006b).

In some embodiments of the invention a solution obtained from process step 005 is passed first through a 300 kDa filter (step 006a) and subsequently collected on a 100 kDa filter (step 006b).

In some embodiments of the invention a solution obtained from process step 005 is passed first through a 50 kDa filter (step 006a) and subsequently collected on a 30 kDa filter (step 006b).

It is advantageous to wash the material with several portions of water after step 006b to further remove residual metal ions, monomers or solvent residues from step 005.

Other ultrafiltration methods such as spin filters or dialysis can also be used in step 006x.

Particles of the desired size range may also be selected by size exclusion chromatography (also called gel filtration) in step 006x.

Optionally, said manganese rich, polymeric phosphonate product may be purified in a step 007. Step 007 may have several substeps 007a, 007b etc of, for a substep in no particular order, 007x.

One preferred method of a purification step 007x is treatment with a small amount of cation exchanger, such as sulfonated polystyrene, to remove excess manganese or loosely bound manganese. Commercially available ion exchange resins often has a capacity of 1-2 mmol/g resin and typically crude material from step b) containing 1 mole of manganese would be treated with 1-100 g of the sodium or potassium form of an ion exchange resin.

In some embodiments of the invention step 007x involves yet another diafiltration collecting the material on a 30 kDa filter.

In some embodiments of the invention process step 007x involves treatment of the product from step 006 with the sodium form of an ion exchange resin of the polystyrene sulfonate type.

Subsequent purification steps 007x to remove lipophilic impurities such as traces of endotoxins (residues of dead bacteria) may also be added.

In some embodiments of the process the product of step 006 is treated with activated charcoal.

In some embodiments the process the product of step 006 is passed through a polyethylene, or polypropylene, or PVDF filter.

In some embodiments of the process the product of step 006 is treated with immobilized polymyxin B.

Optionally, a step 009 may be inserted as indicated in FIG. 1, where a bioinert surface modifier is grafted to the accessible parts of the nanostructure.

Optionally, crosslinking (step 010) may be effected by the incorporation of crosslinking agents at many places in the process as indicated in FIG. 1. Crosslinking by mixing in the crosslinking agent in step 001 is a standard procedure. The monomer may also be inherently prone to crosslinking like the trialkoxy silanes in one of the preferred embodiments of the current invention so that the material formed in step 002 is already crosslinked.

In the third major aspect of the current invention, the material is used as a contrast agent for diagnostic procedures and in particular for magnetic resonance imaging (MRI). The material of the current invention has the properties of low toxicity and high relaxivity which makes it useful as a contrast agent in MRI exams of an organism, in particular of a human body.

The combination of the properties of high relaxivity and of suitable size for those embodiments of the invention where the hydrodynamic diameter is larger than 3 nm or larger than 4 nm or larger than 5 nm makes compositions comprising the nanostructures of the current invention suitable for imaging of tumors, in particular solid tumors by MRI. It is also conceivable to use said compositions of the current invention as a contrast agent for general anatomical imaging e.g. angiography; in particular angiography of the fine coronary arteries of the heart, or angiography of the carotid arteries, or the renal arteries or the aorta, is enabled by the high relaxivity and contrast of the current invention. Imaging of structures in the head, internal organs or extremities are also of interest. Of the internal organs, liver, pancreas and bowels are of particular interest. Imaging of the colon can be achieved either by intravenous administration or administration as an enema. For imaging of the stomach, liver and the upper gut it is conceivable to administer the contrast agent orally.

Because of the low toxicity and high relaxivity of the materials of the current invention, they are useful as cell tagging agents. Cells, like stem cells or macrophages for diagnostic or therapeutic use in a patient are loaded with nanostructures of the current invention ex vivo and subsequently administered to said patient and their distribution in the body may be visualized with MRI In some embodiments of the invention, a solution of the nanostructures is injected into the tissue, often but not limited to, intradermally, or subcutaneously and subsequently used to visualize the lymphatic structures of a patient by MRI. Of particular interest is the imaging of lymph nodes which are a common location of metastatic tumors. Particularly useful for this purpose are nanostructures with sizes around 10 nm, such as 7-50 nm or 7-25 nm or 7-15 nm.

In some embodiments of the current invention a formulation of the nanostructures of the current invention with an average hydrodynamic diameter in the range of 8-15 nm is administered to a patient intradermally and the lymph nodes of said patient are visualized by an MRI procedure.

Since the nanostructures of the current invention has the properties of high relaxivity and low toxicity it is conceivable to use the material for cell tagging. In that case cells e.g. stem cells or macrophages are loaded with nanostructures externally to a mammalian body, e.g. a human body, and then inserted into said mammal and an image is generated by MRI scanning. It is then possible to follow the cells as they are transported through the organism.

The in vivo use of the nanoparticles of this invention requires them to be formulated in a pharmacologically acceptable way according to best practice well known to those skilled in the art. The preferred mode of administration is parenteral, in particular is the intra venous route advantageous but intra arterial may have advantages under certain circumstances. Parenteral administration often requires a liquid formulation. Water is a preferred solvent to bring the nanostructures of the current invention into solution but one or more co-solvents or additives may be added in 0.1-10% to improve stability in solution. Acceptable co solvents are alcohols like ethanol or glycerol, biocompatible polymers like ethyleneglycol or polyvinyl alcohol, dimethyl sulfoxide, or N-methyl pyrrolidinone. It can also be advantageous to add one or more osmoregulators like mannitol, sorbitol, lactose, glucose or other sugars or sugar alcohols. It is desirable that the formulation is isoosmotic with the body fluids. Preferably, the solution for intra venous use has and osmolality from 270-2000 mOsm or 280-1000 mOsm or 280-500 mOsm or in particular from 280-300 mOsm. Many of said additives may also fulfill the function of cryoprotectants, enhancing the efficiency of reconstitution after freeze drying. It may also be advantageous to add electrolytes to lower the physiological effects of the injected solution. Preferred electrolytes would be a combination of non toxic salts of sodium, calcium or and/or magnesium. Regulation of the pH of the injectable solution is preferable and any buffer suitable for injection can be contemplated but preferred is Tris-HCl. Metal ion scavengers can also be contemplated as an additive. Some typical examples would be EDTA (ethylendiaminetetraacetic acid), DTPA (diethylene triamine pentaacetic acid) and DOTA (1,4,7,10-tetraaza-cyclododecane-N,N',N'',N'''-tetraacetic acid) or fodipir. The use of solid-phase ion scavenging resins added to the storage bottle can also be contemplated.

The concentration of nanostructures may be described in many different ways but the two most relevant are mass concentration given as g/l solution and concentration of manganese in mmol/l solution. Concentration ranges of manganese in formulations that are suitable for administration as a contrast agent range from 1-500 mM or 10-300 mM or 10-200 mM or 50-200 mM or 100-200 mM. When given as a mass concentration and assuming that the phosphorus manganese ratio is around 6, the mass concentrations that are suitable for contrast agent formulation range of 0.5-300 g/l, or 5-200 g/l, or 5-250 g/l, or 5-100 g/l, or 100-250 g/l. The mass concentrations roughly match the concentrations given in mM manganese but the correspondence will vary depending on the polymer framework, the degree of crosslinking and the presence of a bioinert coating layer.

One embodiment of the current invention constitutes a pharmaceutically acceptable formulation for intravenous administration titration with a manganese concentration of 100-300 mM and a phosphorus to manganese ratio of 7-20.

Some embodiments of the present invention relates to pharmaceutically acceptable formulations for intravenous administration with a manganese concentration of 10-300 mM and a phosphorus to manganese ratio of 7-20.

An alternative embodiment of the invention is a nanostructure comprising a polymeric framework comprising at least five geminal bisphosphonate groups, wherein the geminal bisphosphonate groups independently of each other are incorporated as

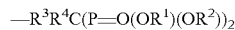

(which is identical to —$R^4R^3C(P=O(OR^1)(OR^2))_2$)

wherein $R^1$ and $R^2$ are independently selected from the group consisting of a negative charge, H, alkyl and aryl, and wherein at least one of $R^3$ and $R^4$ is a group connected to the polymeric framework with the proviso that when only one of $R^3$ and $R^4$ is such a connected group, the other of $R^3$ and $R^4$ is either a group being able to connect to the polymeric framework, or the residue of such a group, or selected from the group consisting of H, OH, $OR^5$ and $R^5$, wherein $R^5$ is a lower alkyl, i.e. a nanostructure as discussed above but not containing any manganese ions. Such a nanostructure is useful as an intermediate in the production of nanostructures according to the previously discussed embodiments. Such a structure may bind other cations than manganese and be useful in that capacity.

BRIEF DESCRIPTION OF THE DRAWINGS

In the examples below reference is made to the appended drawings on which.

EXAMPLES

Example 1

Figure 1:
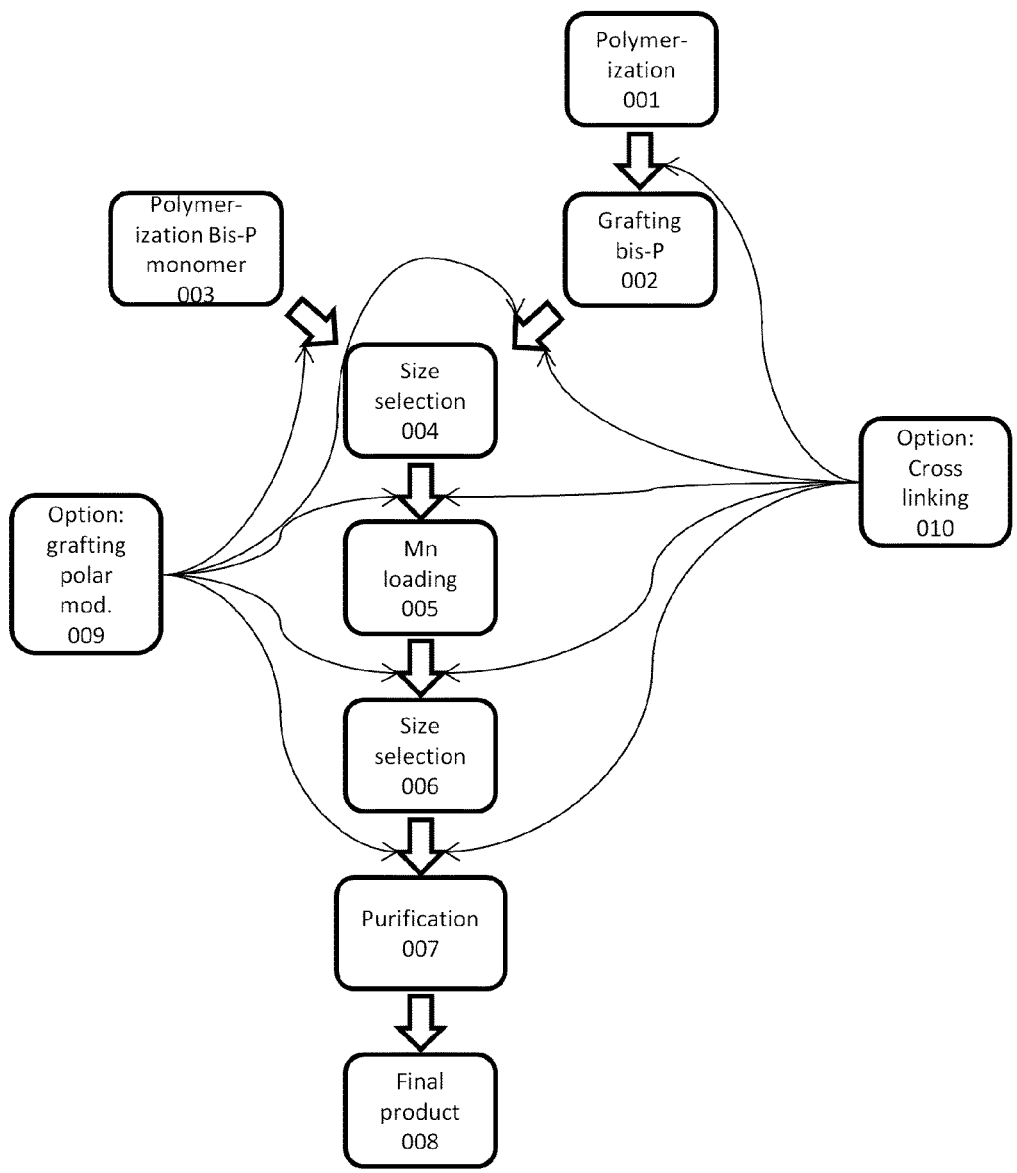
FIG. 1 is a schematic view of a method for obtaining the nanoparticles according to the invention.

Synthesis of Synthesis of 1,1-bis(triethoxysilylpropyl)-1,1-bis(dimethylphosphonato)methane 1a: 1,1-diallyl-1,1-bis(dimethylphosphonato)methane

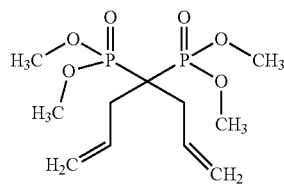

A 2 L reactor fitted with a mechanical stirrer was dried out at 130° C. under vacuum and then allowed to cool under a positive nitrogen pressure. The reactor was charged with dry THF (1 l) (Aldrich dry, 99.9% with 250 ppm BHT) by tube transfer under inert gas. Tetramethylmethylenedi(phosphonate) (97.4 g, 420 mmol) and allyl bromide (183 ml, 255 g, 2.11 mol) were added (no heat evolved, no acidic gas detected). Jacket temperature was set to 0° C. and at an inner temperature of 6° C., was added (split in 6 portions) potassium t-butoxide (140.3 g in total, 1.25 mol). The temperature rose to about 12° C. after each addition and was allowed to go back to 6° C. (or lower) before the next addition. A last addition of allyl bromide (9.4 ml, 0.11 mol) and t-butoxide (7.3 g, 65 mmol) was performed to convert the last few percent of monoallylated product (no exotherm detected). The temperature in the jacket was set to 15° C. for about 2 h and then the thick white reaction mixture was stirred overnight with a jacket temperature of 0° C. The reaction was quenched with 50 ml saturated NH$_4$Cl (aq) (temp raised from 2 to 5° C.) and then toluene (1 l) was added and 1 l was distilled off to drive off THF and excess allylbromide. Collected from 63-73° C. with a jacket temperature from 70-100 degrees over 2 h. To the residue was added silica gel (100 g) and activated charcoal (15 g). The reaction mixture was stirred for a few minutes and the liquid was siphoned off with a frit-filter stick (or filtered through a normal Whatman glass fiber filter). The residual cake was washed with toluene (3×100 ml). The combined filtrate was filtered through a Whatman glass fiber filter to remove the last traces of activated charcoal (indicated by a greenish color) and concentrated on the rotary evaporator (bath temperature 40° C.) to afford the title compound as a pale yellow liquid. The crude product was reintroduced into the cleaned reactor and dissolved in a mixture of toluene (50 ml) and heptane (380 ml). Crystallization can be induced at an inner temperature of 12-9° C. by seeding. The jacket temperature was lowered to −25° C. over a period of 2 h and kept at that temperature for two more hours to complete the crystallization. The mother liquor was removed by a fritted filter stick and the crystal slurry was washed with two portions of pre-cooled heptane (40 ml). The crystals were dissolved in EtOAc and the solution washed out through the bottom valve. The solvent was removed at reduced pressure to give 70.0 g 224 mmol, 53% of the product as a solid with a mp just above room temperature.

$^1$H-NMR (CDCl$_3$); 6.35 (m, 2H), 5.20 (m, 4H), 3.68 (d, 12H), 3.00 (abx, 4H).

It was also possible to distill the product in a short path, thin film distillation apparatus.

1b: 1,1-bis(triethoxysilylpropyl)-1,1-bis(dimethylphosphonato)methane

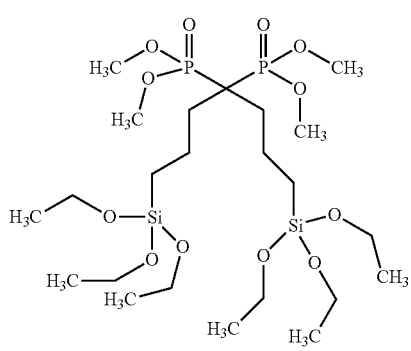 [SMILES: CCO[Si](CCCC(CCC[Si](OCC)(OCC)OCC)(P(=O)(OC)OC)P(=O)(OC)OC)(OCC)OCC]

A 2 l reactor with temperature control jacket, inner thermometer and a mechanical stirrer was charged with toluene (330 ml, Aldrich dry, sure seal capped), tetramethyl-1,1-bis allyl-methylenebis(phosphonate) (70 g, 224 mmol) and triethoxysilane (123 ml, 655 mmol). The reaction mixture was deoxygenated by three vacuum-nitrogen cycles, care taken to keep the vacuum cycles short to avoid loss of toluene and silane. Oxygen is critical to remove. The jacket temperature was set to 30° C. Karstedt's catalyst (4.5 ml, 2% in toluene 0.053 mmol) was syringed in as 0.5 ml portions with 30 minutes between (4.5 h total). After the additions of catalyst were completed the temperature control jacket was set to 30° C. and the mixture was left to stir overnight. The next morning the jacket temperature was set to 40 degrees, a distillation head added and the toluene and excess silane distilled off at a pressure from 62 to 13 mbar. Duration 2 h. Ethanol (800 ml) and activated charcoal (15 g) was added and the slurry was stirred for 10 min. and the mixture was taken out through the bottom valve and filtered through a Whatman glass fiber filter. The solvent was removed at reduced pressure on a rotary evaporator until constant weight (bath temperature 45° C.) to give 138 g (215 mmol, 96%) of the product as a pale brown oil.

$^1$H-NMR (CDCl$_3$); 3.95 (q, 12H), 3.77 (d, 12H), 2.37 (m, 4H), 2.12 (m, 4H), 1.32 (t, 18H), 0.88 (t, 4H).

It was also possible to distill the product in a short path, thin film distillation apparatus at 170° C. and 0.3 mbar.

Example 2

Synthesis of 1,1-bis(2-trimethoxysilylethyl)-1,1-bis(dimethylphosphonato)methane

2a: 1,1-bis(2-t-butoxyethyl)-1,1-bis(dimethylphosphonato)methane

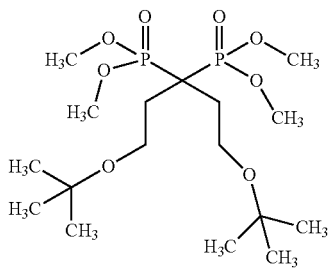 [SMILES: COP(=O)(OC)C(CCOC(C)(C)C)(CCOC(C)(C)C)P(=O)(OC)OC]

To an ice cooled solution of 1,1-bis(dimethyl)phosphonato)methane (50 g, 215 mmol) in dry THF (500 ml) under nitrogen is added sodium hydride (18.9 g, 60% in mineral oil, 474 mmol) in three portions, over 30 minutes. The mixture is stirred for 3 hours and then 1-bromo-2-t-butoxyethane (90.5 g, 500 mmol) is added in 5 ml portions. The ice bath is removed after three hours and stirring continued at room temperature for overnight. The reaction mixture is cooled with an ice bath again and quenched by the addition of 50 ml saturated aqueous ammonium chloride. The volatiles are removed in vacuo and the organics are dissolved in dichloromethane (300 ml). Silica (100 g) is stirred in and the slurry is filtered and the filter cake is washed with 3×200 ml dichloromethane. The product is obtained after removal of the solvents.

2b: 1,1-bis(2-hydroxyethyl)-1,1-bis(dimethylphosphonato)methane

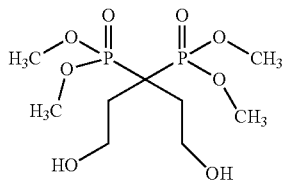

Trifluoroacetic acid (TFA, 50 ml) and dichloromethane (DCM, 50 ml) is added to 2 g of 1,1-bis(2-t-butoxyethyl)-1,1-bis(dimethylphosphonato)methane (example 2a). The mixture is stirred at room temperature for 1 h and the volatiles are removed at reduced pressure to give the product.

2c: Synthesis of 1,1-bis(2-mesyloxyethyl)-1,1-bis(dimethylphosphonato)methane

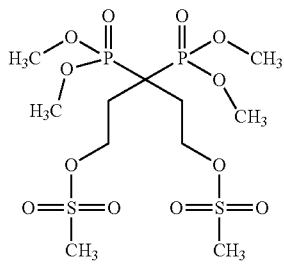

The product of example 2b (1,1-bis(2-hydroxyethyl)-1,1-bis(dimethylphosphonato)methane) (10 mmol) is dissolved in ice cooled dichloromethane (10 ml). Pyridine (40 mmol, 3.24 ml) and methanesulfonylchloride (3.44 g, 30 mmol) are added, the latter while keeping the inner temperature<5° C. After three hours ether (30 ml) and water (7 ml) are added. After phase separation, the organic layer is washed with 2 M HCl, 5% aqueous sodium hydrogen carbonate and water. Drying over magnesium sulfate is followed by evaporation of the volatiles to yield the product.

2d: 1,1-divinyl-1,1-bis(dimethylphosphonato)methane

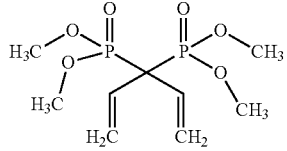

To an ice cooled solution of 1,1-bis(2-mesyloxyethyl)-1,1-bis(dimethylphosphonato)methane (50 g, 104 mmol) in dry THF (500 ml) under nitrogen is added diethylisopropylhylamine (300 mmol). The ice bath is removed after 30 minutes and stirring continued at room temperature overnight. The volatiles are removed in vacuo and the organics are dissolved with ether (300 ml). Silica (100 g) and activated charcoal (15) is stirred in and the slurry is filtered and the filter cake is washed with 3×200 ml ether. The product is obtained after removal of the solvent.

2e: 1,1-bis(2-trimethoxysilylethyl)-1,1-bis(dimethylphosphonato)-methane

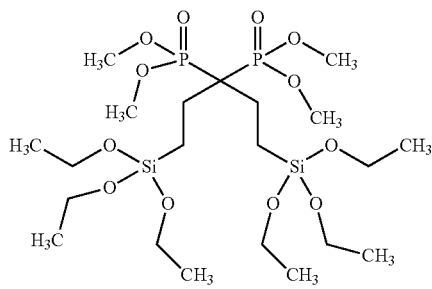 [SMILES: CCO[Si](CCC(CC[Si](OCC)(OCC)OCC)(P(=O)(OC)OC)P(=O)(OC)OC)(OCC)OCC]

To a solution of 1,1-divinyl-1,1-bis(dimethylphosphonato)methane (Example 2d) (2.0 mmol) in dry toluene (20 ml) is added 80 µl of a solution of Karstedt's catalyst in toluene (2% Pt) and triethoxysilane (6.0 mmol, 4.1 ml). The solution is left at room temperature for 2 days. The volatiles are removed in vacuo and the residual silane is removed by two more addition-of-toluene-vacuum cycles. The residue is taken up in toluene, treated with a small amount of activated charcoal, passed through a 5 µm PTFE filter and purified by flash chromatography on a silica column with dichloromethane+0-10% methanol as the eluent to yield the desired product.

Example 3

Synthesis of 1,1-bis(trimethoxysilylmethyl)-1,1-bis(dimethylphosphonato)methane

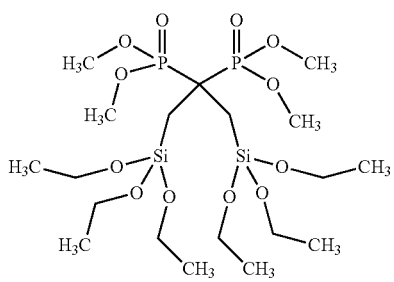 [SMILES: CCO[Si](CC(C[Si](OCC)(OCC)OCC)(P(=O)(OC)OC)P(=O)(OC)OC)(OCC)OCC]

To an ice cooled solution of 1,1-bis(dimethyl)phosphonato)methane (50 g, 215 mmol) in dry THF (500 ml) under nitrogen is added sodium hydride (18.9 g, 60% in mineral oil, 474 mmol) in three portions, over 30 minutes. The mixture is stirred for 3 hours and then chloromethyltriethoxysilane (500 mmol) is added in portions, maintaining the inner temperature below 5° C. The ice bath is removed after three hours and stirring continued at room temperature for overnight. The reaction mixture is cooled with an ice bath again and quenched by the addition of 50 ml saturated aqueous ammonium chloride. The volatiles are removed in vacuo and the organics are dissolved in dichlormethane (300 ml). Silica (100 g) is stirred in and the slurry is filtered and the filter cake is washed with 3×200 ml dichloromethane. The product is obtained after removal of the solvents.

Example 4

Synthesis of 1,1-bis(3-trimethoxysilylpropyl)-1,1-bis(diethylphosphonato)methane 4a: 1,1-diallyl-1,1-bis(diethylphosphonato)methane

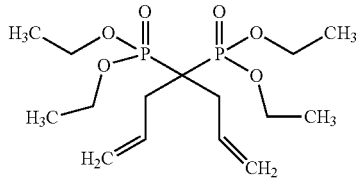 [SMILES: C=CCC(CC=C)(P(=O)(OCC)OCC)P(=O)(OCC)OCC]

To an ice cooled solution of 1,1-bis(diethyl)phosphonato)methane (4.97 ml, 20 mmol) in dry THF (50 ml) under nitrogen was added allyl bromide (8.7 ml, 100 mmol). Over a period of two hours was added potassium tert-butoxide (6.8 g, 60 mmol). The solution was stirred at room temperature overnight and then quenched by the addition of 50 ml saturated aqueous ammonium chloride. The volatiles were removed in vacuo and the organics were dissolved with dichlormethane. Flash chromatography on silica in dichloromethane+methanol (0-10% gradient) gave essentially pure product (NMR).

4b: 1,1-bis(3-trimethoxysilylpropyl)-1,1-bis(diethylphosphonato)methane

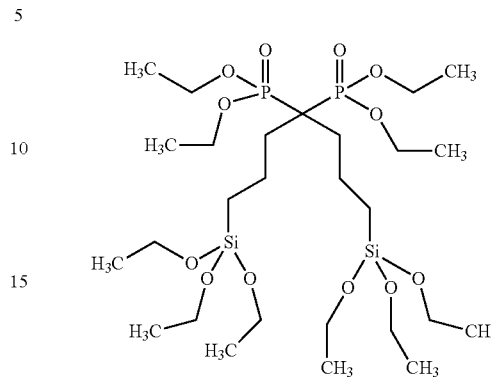

To a solution of 1,1-diallyl-1,1-bis(diethylphosphonato)methane (Example 2a) (4.4 g, 14.2 mmol) in dry toluene (25 ml) was added 212 μl of a solution of Karstedt's catalyst in toluene (2% Pt) and triethoxysilane (42.7 mmol, 7.8 ml). The solution was left at room temperature overnight. The volatiles were removed in vacuo and the residual silane was removed by two more addition-of-toluene-vacuum cycles. The residue was taken up in toluene, treated with a small amount of activated charcoal, passed through a 5 μm PTFE filter and purified by flash chromatography on a silica column with dichloromethane+0-10% methanol as the eluent. Yield: 6.9 g of material with 90% NMR purity.

Example 5

Synthesis of 1,1-bis(3-trimethoxysilylpropyl)-1,1-bis(diisopropylphosphonato)methane 5a: 1,1-diallyl-1,1-bis(diisopropylphosphonato)methane

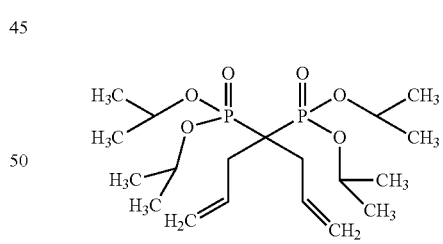

To an ice cooled solution of 1,1-bis(diisopropyl)phosphonato)methane (6.44 ml, 20 mmol) in dry THF (50 ml) under nitrogen was added allyl bromide (8.7 ml, 100 mmol). Over a period of two hours was added potassium tert-butoxide (6.8 g, 60 mmol). The solution was stirred at room temperature overnight and then quenched by the addition of 50 ml saturated aqueous ammonium chloride. The volatiles were removed in vacuo and the organics were dissolved with dichlormethane. Flash chromatography on silica in Dichloromethane+methanol (0-10% gradient) gave 6.5 g of essentially pure product (NMR).

5b: 1,1-bis(3-trimethoxysilylpropyl)-1,1-bis(diisopropylphosphonato)-methane

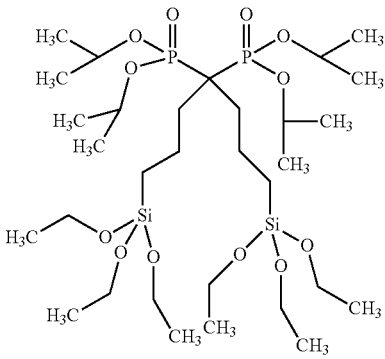 [SMILES: CCO[Si](CCCC(CCC[Si](OCC)(OCC)OCC)(P(=O)(OC(C)C)OC(C)C)P(=O)(OC(C)C)OC(C)C)(OCC)OCC]

To a solution of 1,1-diallyl-1,1-bis(diisopropylphosphonato)methane (Example 2a) (0.736 g, 2.0 mmol) in dry toluene (20 ml) was added 80 µl of a solution of Karstedt's catalyst in toluene (2% Pt) and triethoxysilane (6.0 mmol, 4.1 ml). The solution was left at room temperature for 2 days. The volatiles were removed in vacuo and the residual silane was removed by two more addition-of-toluene-vacuum cycles. The residue was taken up in toluene, treated with a small amount of activated charcoal, passed through a 5 µm PTFE filter and purified by flash chromatography on a silica column with dichloromethane+0-10% methanol as the eluent. Yield: 1.0 g of material with 90% NMR purity.

Example 6

Synthesis of 1,1-bis(3-trimethoxysilylpropyl)-1,1-bis(di-(3-methoxyphenylyl)phosphonato)methane 6a: 1,1-bis(di-(3-methoxyphenylyl)phosphonato)methane

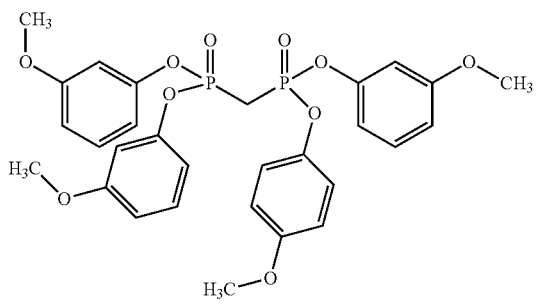 [SMILES: COc1ccc(OP(=O)(CP(=O)(Oc2cccc(OC)c2)Oc2cccc(OC)c2)Oc2cccc(OC)c2)cc1]

To an ice cooled solution of bis(dichlorophosphonato)methane in dry dichloromethane (50 ml) was added 3-methoxyphenol (1.76 ml, 16 mmol). A solution of triethyl amine (4.91 ml, 32 mmol) was added over a period of 1 h. The reaction mixture was then stirred at room temperature for four hours whereupon it was poured out on ice water (150 ml). Dichloromethane was added and the phases were separated (slow!). The aqueous phase was extracted once more with dichloromethane and the combined organic phases were dried over sodium sulfate. After evaporation the crude product was purified by flash chromatography on silica (column height 10 cm, diameter 3 cm). The product was obtained as a pale brown oil and NMR spectroscopy indicated high purity. Yield 0.93 g.

6b: 1,1-diallyl-1,1-bis(di-(3-methoxyphenylyl)phosphonato)methane

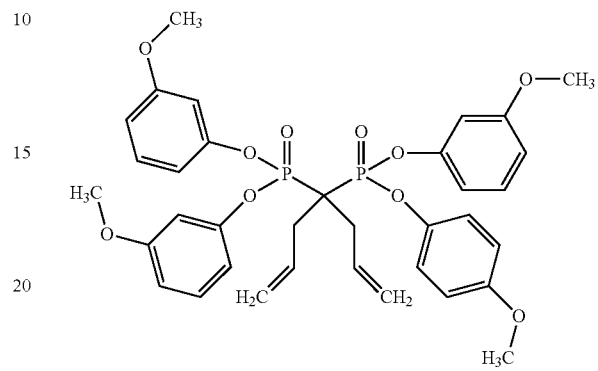

Sodium hydride (0.683 g 60% in mineral oil, 17.1 mmol) was suspended in dry THF (150 ml) and cooled to −30° C. A solution of 1,1-bis(di-(3-methoxyphenylyl)phosphonato)methane (example 4a, 2.92 g, 4.87 mmol) in dry THF was added over 30 minutes while maintaining the temperature at −30° C. Allylbromide (48.8 mmol, 4.21 ml) was added and the reaction mixture was kept at −15° C. for one hour, then heated to 40° C. for 5 days. The contents were added to 75 ml saturated aqueous ammonium chloride. The volatiles were evaporated at reduced pressure and the solids were triturated with dichloromethane to extract the organics. After drying over sodium sulfate and evaporation of the solvent, the crude product was purified by flash chromatography on silica with heptane:ethyl acetate 6:4 as the eluent. Yield 1.28 g.

6c: 1,1-bis(3-trimethoxysilylpropyl)-1,1-bis(di-(3-methoxyphenylyl)-phosphonato)methane

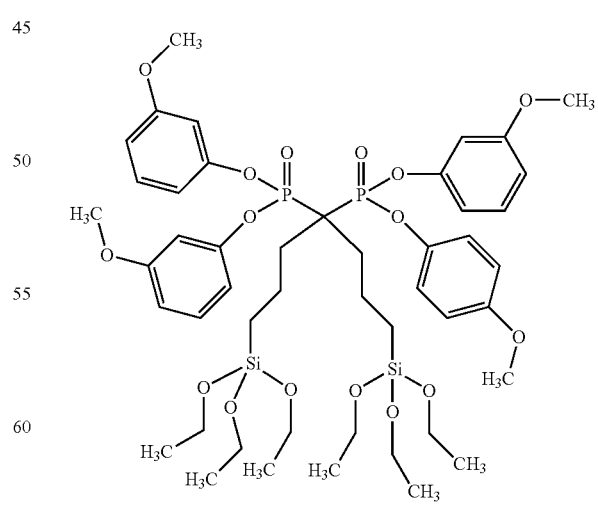

To a solution of 1,1-diallyl-1,1-bis(di-(3-methoxyphenylyl)phosphonato)methane (Example 4b) (0.794 g, 1.16 mmol) in dry toluene (20 ml) was added 50 µl of a solution of Karstedt's catalyst in toluene (2% Pt) and triethoxysilane (1.16 mmol, 0.459 ml). The solution was left at room temperature for 4 days and every day an addition of yet 0.7 g of the silane and 25 µl of the catalyst was made. The volatiles were removed in vacuo and the residual silane was removed by two more addition of toluene-vacuum cycles. The residue was taken up in toluene, treated with a small amount of activated charcoal, passed through a 5 µm PTFE filter and purified by flash chromatography on a silica column with ethyl acetate:toluene 1:1 as the eluent. Yield 150 mg.

Example 7

Synthesis of 1,1-bis(3-trimethoxysilylpropyl)-1,1-bis(dicyclopropylmethyl)phosphonato)methane 7a:
1,1-bis(di-cyclopropylmethyl)phosphonato)methane

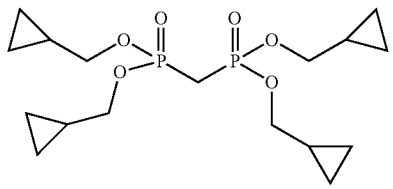 [SMILES: O=P(CP(=O)(OCC1CC1)OCC1CC1)(OCC1CC1)OCC1CC1]

To an ice cooled solution of bis(dichlorophosphonato)methane (1.00 g) in dry dichloromethane (50 ml) was added cylclopropylmethanol (1.15 g, 16 mmol). A solution of triethyl amine (4.91 ml, 32 mmol) was added over a period of 1 h. The reaction mixture was then stirred at room temperature for four hours whereupon it was poured out on ice water (150 ml). Dichloromethane was added and the phases were separated (slow!). The aqueous phase was extracted once more with dichloromethane and the combined organic phases were dried over sodium sulfate. After evaporation the crude product was purified by flash chromatography on silica (column height 10 cm, diameter 3 cm). The product was obtained as a colorless oil and NMR spectroscopy indicated high purity. Yield 1.04 g, 66%.

7b: 1,1-diallyl-1,1-bis(di-(cyclopropylmethyl)phosphonato)methane

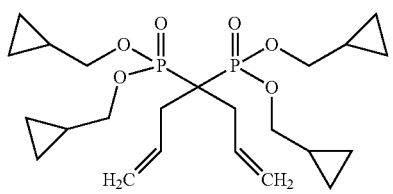 [SMILES: C=CCC(CC=C)(P(=O)(OCC1CC1)OCC1CC1)P(=O)(OCC1CC1)OCC1CC1]

To an ice cooled solution of 1,1-bis(di-cyclopropylmethyl)-phosphonato)methane (Example 5a) (0.794 g, 1.16 mmol) in dry THF (20 ml) under nitrogen was added allyl bromide (0.864 ml, 10 mmol). Over a period of two hours was added potassium tert-butoxide (0.66 g). The solution was stirred at room temperature for 4 h and then quenched by the addition of 3 ml saturated aqueous ammonium chloride. The volatiles were removed in vacuo and the organics were dissolved with dichloromethane. Flash chromatography on silica in heptane:ethyl acetate 3:7 gave 0.4 of pure product. 64%.

7c: 1,1-bis(3-triethoxysilylpropyl)-1,1-bis(di-cyclopropylmethyl)-phosphonato)methane

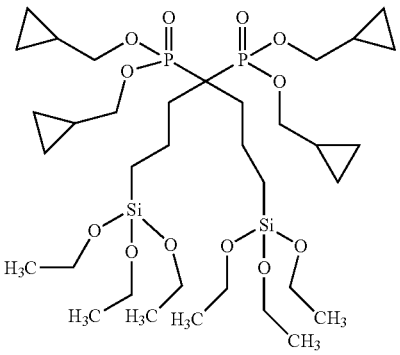 [SMILES: CCO[Si](CCCC(CCC[Si](OCC)(OCC)OCC)(P(=O)(OCC1CC1)OCC1CC1)P(=O)(OCC1CC1)OCC1CC1)(OCC)OCC]

To a solution of 1,1-diallyl-1,1-bis(di-(cyclopropylmethyl)phosphonato)-methane (Example 5b) (0.373 g, 0.76 mmol) in dry toluene (20 ml) was added 30 µl of a solution of Karstedt's catalyst in toluene (2% Pt) and triethoxysilane (1.59 mmol, 0.299 ml). The solution was left at room temperature for 4 days and every day an addition of yet 0.15 ml of the silane and 15 µl of the catalyst was made. The volatiles were removed in vacuo and the residual silane was removed by two more addition of toluene-vacuum cycles. The residue was taken up in toluene, treated with a small amount of activated charcoal, passed through a 5 PTFE filter and purified by flash chromatography on a silica column with dichloromethane+5% methanol as the eluent. Yield 376 mg.

Example 8

Synthesis of a nanostructure Y1 conjugated to N-(2-aminoethyl)-16,16-di-2,5,8,11,14-pentaoxapentadecyl-2,5,8,11,14,18-hexaoxaicosan-20-oic amide Example 8a 3-(3-bromo-2,2-bis(bromomethyl)propoxy)prop-1-ene

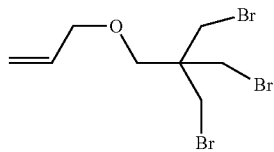

Sodium hydride (1.67 g, 42 mmol) was added carefully to 3-bromo-2,2-bis(bromomethyl)propanol (9.75 g, 30 mmol) and allyl bromide (12.9 ml, 150 mmol) in dry and degassed DMF (40 ml) under nitrogen at 0° C. The temperature was then increased to room temperature (22° C.) and the reaction mixture was stirred for another 3 h. The reaction mixture was then carefully added to an aqueous saturated NH$_4$Cl (50 ml). The H$_2$O-phase was then extracted with diethyl ether (2×50 ml) and the combined organic phases were washed with H$_2$O (5×50 ml) and then brine (50 ml). The organic phase was dried with Na$_2$SO$_4$ followed by filtration. The volatile materials were removed at reduced pressure to give a pale yellow oil (9.7 g). Column chromatography on silica (heptane:EtOAc 9:1) gave 6.6 g (62%) of the product as a clear oil. $^1$H-NMR (CDCl$_3$); 5.93 (m, 1H), 5.28 (m, 2H), 4.05 (d, 2H), 3.58 (s, 6H), 3.52 (s, 2H).

Example 8b 16-(allyloxymethyl)-16-2,5,8,11,14-pentaoxapentadecyl-2,5,8,11,14,18,21,24,27,30-decaoxahentriacontane

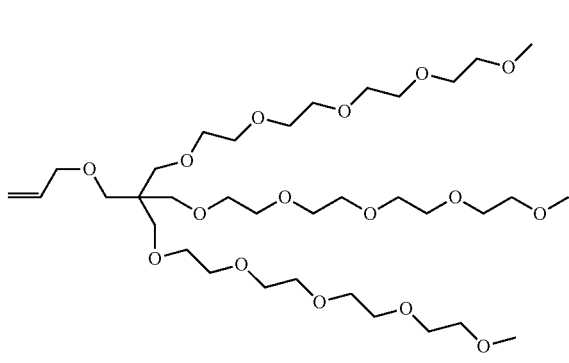 [SMILES: C=CCOCC(COCCOCCOCCOCCOC)(COCCOCCOCCOCCOC)COCCOCCOCCOCCOC]

Tetraethyleneglycol monomethyl ether (1.91 ml, 9 mmol) dissolved in dry and degassed DMF (3.5 ml, dried 24 h, 4 Å MS) was added carefully to sodium hydride (365 mg, 9 mmol) in dry and degassed DMF (15 ml, dried 24 h, 4 Å MS) under nitrogen at 0° C. using a syringe. The temperature was then raised to room temperature and the reaction mixture was stirred for another 30 min. 3-(3-bromo-2,2-bis(bromomethyl)propoxy)prop-1-ene (730 mg, 2.0 mmol) was then added and the temperature was raised to 100° C. After 14 h the reaction was completed (HPLC-ELSD-C18, 95:5 to 5:95 H$_2$O/ACN in 25 min, R$_t$ product=19.5 min) the temperature was decreased to room temperature and the reaction mixture was carefully added to H$_2$O (150 ml) and the H$_2$O-phase was washed with diethyl ether (2×50 ml). Sodium chloride was then added to the H$_2$O-phase until saturation. The H$_2$O-phase was extracted with EtOAc (4×50 ml) and the combined organic phases were washed with brine (2×30 ml). Sodium sulfate and charcoal was added to the organic phase. The clear organic phase was filtered and the volatile material was removed at reduced pressure (8 mm Hg, 40° C. then 0.1 mm Hg (oil pump) and 40° C. to remove residual DMF). Column chromatography (EtOAc:MeOH 9:1) gave 1.05 g (70%) of the product. $^1$H-NMR (CDCl$_3$); 5.90 (m, 1H), 5.20 (m, 2H), 3.94 (dt, 2H), 3.70-3.55 (m, 48H), 3.45 (s, 6H), 3.43 (s, 2H), 3.40 (s, 9H).

Example 8c 16,16-di-2,5,8,11,14-pentaoxapentadecyl-2,5,8,11,14-pentaoxaheptadecan-17-ol (4)

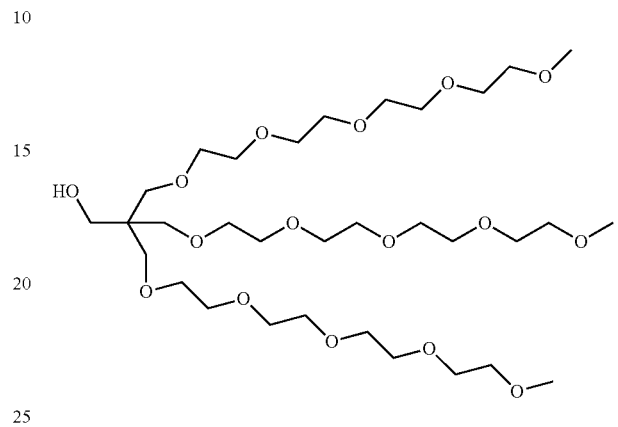

Potassium tert-butoxide (74 mg, 0.66 mmol) was added to 2 (500 mg, 0.66 mmol) in DMSO (3 ml). The reaction mixture was shaken at 100° C. for 15 min. HPLC analysis (HPLC-ELSD-C18, 95:5 to 5:95 H$_2$O/ACN in 25 min) indicated complete conversion to the product. Brine (20 ml) was added at room temperature and the aqueous phase was extracted with ethyl acetate (3×20 ml). The combined organic phases were washed with brine (3×20 ml) and the dried with sodium sulfate. Filtration and removal of volatile material at reduced pressure gave 16-2,5,8,11,14-pentaoxapentadecyl-16-((prop-1-enyloxy)methyl)-2,5,8,11,14,18,21,24,27,30-decaoxahentriacontane as a clear oil. HCl (0.1 M) was then added to the oil dissolved in acetone (4 ml) and the mixture was shaken at 55° C. for 30 min. The volatile material was then removed at reduced pressure, which gave 420 mg (89%) of 4 as a clear oil. $^1$H-NMR (CDCl$_3$); 3.66-3.52 (m, 48H), 3.47 (s, 6H), 3.37 (s, 9H).

Example 8d tert-butyl 16,16-di-2,5,8,11,14-pentaoxapentadecyl-2,5,8,11,14,18-hexaoxaicosan-20-oate (5)

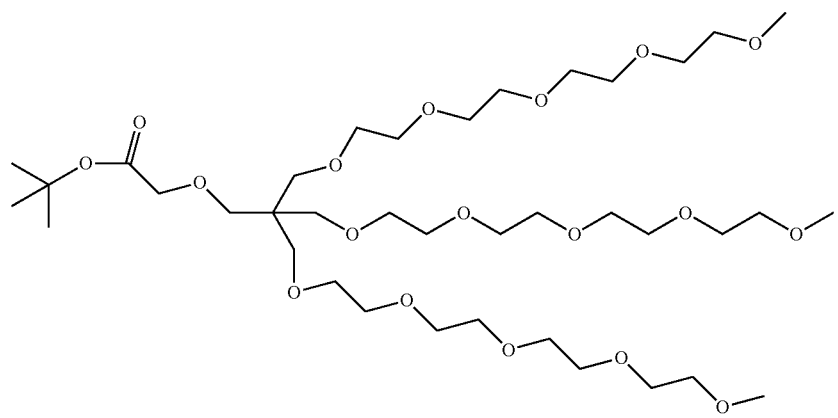 [SMILES: COCCOCCOCCOCCOCC(COCCOCCOCCOCCOC)(COCCOCCOCCOCCOC)COCC(=O)OC(C)(C)C]

Potassium tert-butoxide (32 mg, 0.28 mmol) was added to 4 (100 mg, 0.14 mmol) and tert-butyl-2-bromo acetate (105 mg, 0.54 mmol) in dry THF (3 ml). The reaction mixture was shaken for 30 min. Diethyl ether (10 ml and brine (5 ml) were added and the aqueous phase was extracted with ethyl acetate (3×20 ml). The combined organic phases were washed with brine and then dried with sodium sulfate. The volatile material was removed at reduced pressure and the crude product was purified by column chromatography (ethyl acetate/methanol 9:1), which gave 60 mg (52%) of 5. $^1$H-NMR (CDCl$_3$); 3.91 (s, 2H), 3.66-3.52 (m, 48H), 3.51 (s, 2H), 3.45 (s, 6H), 3.37 (s, 9H), 1.46 (s, 9H).

Example 8e 16,16-di-2,5,8,11,14-pentaoxapentadecyl-2,5,8,11,14,18-hexaoxaicosan-20-oic acid (6)

2-(1H-Benzotriazol-1-yl)-1,1,3,3-tetramethyluronium hexafluorophosphate (95 mg, 0.25 mmol) was added to 16,16-di-2,5,8,11,14-pentaoxapentadecyl-2,5,8,11,14,18-hexaoxaicosan-20-oic acid (Example 8e) (153 mg, 0.2 mmol), N-BOC-ethylenediamine (40 mg, 0.25 mmol) and diisopropylethylamine (87 μl, 0.5 mmol) in DMF (1 ml, dried 4 Å MS and degassed) at room temperature under nitrogen. The reaction mixture was shaken for 20 h. Diethyl ether was added to the reaction mixture and the mixture was extracted 3 times with H$_2$O. The combined aqueous phases were saturated with NaCl (s) and then extracted 4 times with EtOAc. The combined organic phases were dried with Na$_2$SO$_4$, filtered and the solvent was removed at reduced pressure to give 190 mg (quant) of the product as a pale yellow oil. HPLC analysis (HPLC-ELSD-C18, 90:10 to 5:95 TFA 0.1% in H$_2$O/ACN in 20 min) displayed a single peak at 14.5 min.

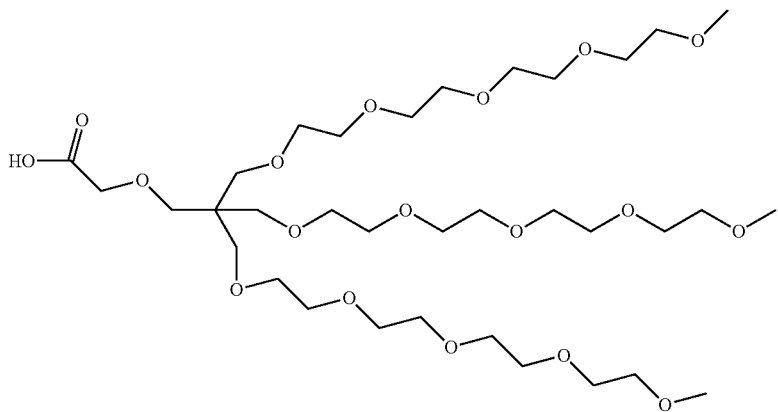 [SMILES: COCCOCCOCCOCCOCC(COCCOCCOCCOCCOC)(COCCOCCOCCOCCOC)COCC(=O)O]

Trifluoroacetic acid (TFA, 0.5 ml) and dichloromethane (0.5 ml) was added to 20 mg of 5. The mixture was shaken at room temperature for 1 h and the volatile materials was then removed at reduced pressure to give 18 mg of 6 as a yellow oil.

Example 8f

N-(2-t-butoxycarbonylamidoethyl)-16,16-di-2,5,8,11,14-pentaoxapentadecyl-2,5,8,11,14,18-hexaoxa-icosan-20-oic amide

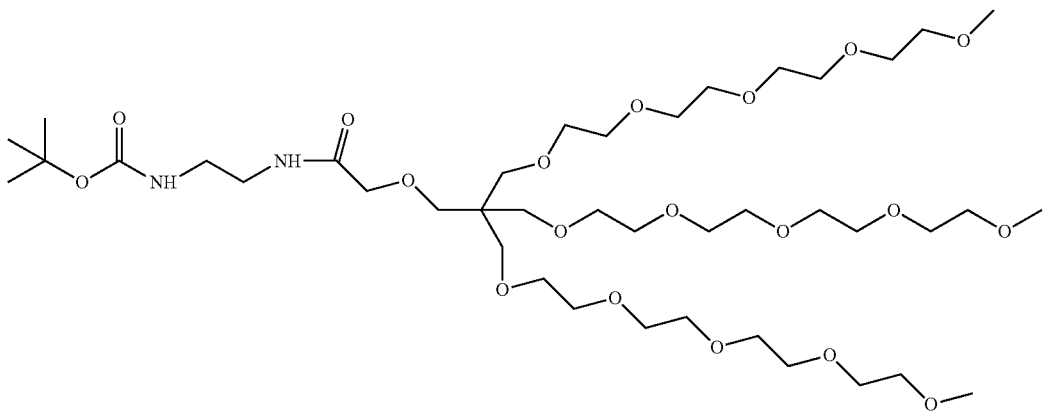 [SMILES: COCCOCCOCCOCCOCC(COCCOCCOCCOCCOC)(COCCOCCOCCOCCOC)COCC(=O)NCCNC(=O)OC(C)(C)C]

Example 8g

N-(2-aminoethyl)-16,16-di-2,5,8,11,14-pentaoxapentadecyl-2,5,8,11,14,18-hexaoxaicosan-20-oic amide

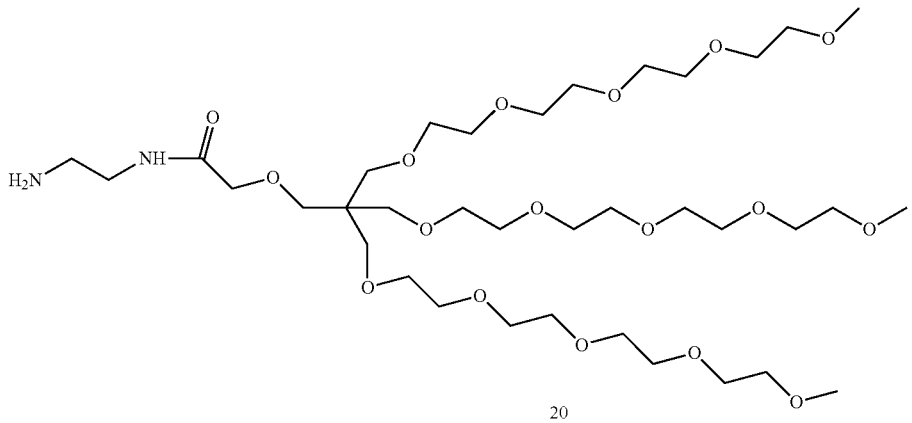

TFA (2 ml) was added to N-(2-t-butoxycarbonylamidoethyl)-16,16-di-2,5,8,11,14-pentaoxapentadecyl-2,5,8,11,14,18-hexaoxaicosan-20-oic amide (example 8f, 160 mg, 0.18 mmol) in dichloromethane (2 ml). The mixture was stirred for 1 h at room temperature. The volatile components were removed at reduced pressure and the residue was co-evaporated twice with dry toluene ($Al_2O_3$) and then dried using an oil pump. This gave 130 mg of the product. HPLC analysis (HPLC-ELSD-C18, 90:10 to 5:95 TFA 0.1% in $H_2O$/MeCN in 20 min) displayed a single peak at 10.7 min. MS (ESP+) [M]: 807.5.

Example 8h

Conjugation

Nanostructure X1 (example 10c, 100 mg, 0.4 mmol P eq) was dissolved in $H_2O$ (2 ml) by sonication. The pH was adjusted from 1.9 to 10.4 using 6 and 1 M NaOH (aq). Manganese chloride (12.5 mg, 0.065 mmol) dissolved in $H_2O$ (2 ml) was then added. The mixture was shaken for 30 min at 30° C. The pH was adjusted from 8.5 to 7.1 using 0.1 HCl (aq) and the material from example 8g (37 mg, 0.04 mmol) and N-hydroxysulfosuccinimide sodium salt (9 mg, 0.04 mmol) were added dissolved in $H_2O$ (2 ml). N-(3-dimethylaminopropyl)-N'-ethylcarbodiimide hydrochloride (24 mg, 0.12 mmol) was then added. The reaction mixture was shaken at room temperature for 21 h and then filtered (5 um tubefilter). The filtrate was spin filtered (10 k cut off, 3000 G for 30 min) and the concentrate (4 ml) was diluted to 15 ml using $H_2O$. This procedure was repeated 4 times. The pH of the concentrate (4 ml) was adjusted from 4.7 to 7.1 using 0.1 M NaOH (aq). The filtrate was spin filtered (10 k cut off, 3000 G for 15 min) and the concentrate (0.5 ml) was diluted to 4 ml using $H_2O$. This procedure was repeated 4 times. The final concentrate was filtered (syringe filter 0.2 um) and diluted to 2 ml using $H_2O$. Volume particle size distribution=4-5 nm. GPC analysis (Superose 12 10/300 GL, 100 mM $NH_4CO_3$, pH=7.4, flow 1 ml/min) $R_t$=10.3 min

Example 9

Synthesis of Polyethyleneimine-bisphosphonate nanostructure Z

Example 9a 3,3-Bis(dimethoxyphosphoryl)propanoic acid t-butyl ester

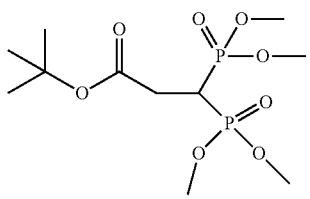 [SMILES: COP(=O)(OC)C(CC(=O)OC(C)(C)C)P(=O)(OC)OC]

To an ice cooled solution of bis(dimethoxyphosphoryl)methane (4.64 g, 20 mmol) and tert-butyl bromoacetate (7.35 ml, 50 mmol) in dry THF (40 ml) under nitrogen was added potassium tert-butoxide (5.8 g, 43 mmol). The reaction mixture was stirred at room temperature overnight and then quenched with 4 ml of saturated ammonium chloride. The volatiles were removed in vacuum and by two cycles of toluene addition and evaporation. Flash chromatography in dichloromethane:methanol, 95:5 on gave the product as an oil. Yield 4.0 g.

Example 9b 3,3-Bis(dimethoxyphosphoryl)propanoic acid

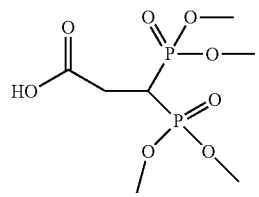 [SMILES: COP(=O)(OC)C(CC(=O)O)P(=O)(OC)OC]

To a solution of 3,3-bis(dimethoxyphosphoryl)propanoic acid t-butyl ester (2.5 g) in dichloromethane (10 ml) was added trifluoroacetic acid. Stirring at room temperature was followed by evaporation of the volatiles in vacuo. Three cycles of vacuum evaporation of 5 ml portions of toluene gave 2.2 g product.

Example 9c

Synthesis of Polyethyleneimine-bisphosphonate nanostructure Z

Branched polyethyleneimine with an average molecular weight of 25 kDa (100 mg, 2.5 mmol primary amino groups), 3,3-bis(dimethoxyphosphoryl)propanoic acid (1.1 g, 3.87 mmol) and N-hydroxysulfosuccinimide sodium salt (100 mg, 0.46 mmol) were dissolved in $H_2O$ (10 ml) by sonication (10 min). The pH was adjusted from 1.8 to 6.5 using 1M NaOH whereupon N-(3-dimethylaminopropyl)-N'-ethylcarbodiimide hydrochloride (1.0 g, 5.2 mmol) was added. The reaction mixture was shaken at room temperature for 23 h and then filtered (5 μm syringe filter). The filtrate was spin filtered (10 k cut off, 3000G for 30 min) and the retentate (2 ml) was diluted to 10 ml using $H_2O$. This procedure was repeated 4 times. The final retentate (2 ml) was diluted to 6 ml using H₂O. Volume average particle size distribution according to DLS: 4-5 nm. GPC analysis (Superose 12 10/300 GL, 100 mM NH₄CO₃, pH=7.4, flow 1 ml/min) Rt=9.1 min.

Example 10

Polymerization of 1,1-bis(triethoxysilylpropyl)-1,1-bis(dimethylphosphonato)methane to yield nanostructures X 1,1-Bis(triethoxysilylpropyl)-1,1-bis(dimethylphosphonato)methane(x g, y mmol, see Table 1 below) was dissolved in 200 ml aqueous 80% 1-propanol in a pressure vessel. The reaction mixture was stirred for 48 h at 95° C. and then for 24 h at 110° C. After allowing the clear solution to cool to room temperature it was diluted with MilliQ H₂O (800 ml) and then diafiltered filtered using 300 k Nominal Molecular Weight Cut-off (NMWC) pore-size column (GE Heathcare's Midgee ultrafiltration cartridge Model: UFP-300-C-3MA). The collected permeates (~980 ml) were then collected on a 100 k NMWC pore size diafilter column (GE Heathcare's Midgee ultrafiltration cartridge Model: UFP-100-C-3MA) to concentrate the nanostructure solution. Alternatively, filters from Pall Life Sciences has also been used, specifically Centramate T-Series cassettes OS0100T02 (100 k NMWC pore size cassette). Repeated addition of MilliQ water and filtration of the collected retentate was done. Final volume of the retentate (X1) collected was about 50 ml.

Furthermore, the permeate that passed through the 100 k diafilter column was collected and then filtered using a 30 k NMWC pore size filter cartridge (GE Heathcare's Midgee ultrafiltration cartridge Model: UFP-30-C-3MA). Repeated addition (2x) of MilliQ water and filtration of the collected retentate was done. Final volume of the retentate (X2) collected was about 50 ml.

Example 10a

Polymerization of 100 mM 1,1-bis(triethoxysilylpropyl)-1,1-bis(dimethylphosphonato)methane X1a. Amounts: x=12.8 g, y=20 mmol. Recovery after diafiltration=26% (based on P recovery); Final pH~2; GPC analysis (Superose 12 10/300 GL, 100 mM NH₄CO₃, pH=7.4, flow 1 ml/min) $R_t$=9.2 min; Composition (ICP, mole ratio): P/Si=0.9.

X2a. Amounts: x=12.8 g, y=20 mmol. Recovery after diafiltration=17% (based on P recovery); Final pH~2; GPC analysis (Superose 12 10/300 GL, 100 mM NH₄CO₃, pH=7.4, flow 1 ml/min) $R_t$=10.3 min; Composition (ICP, mole ratio): P/Si=0.9.

Example 10b

Polymerization of 80 mM 1,1-bis(triethoxysilylpropyl)-1,1-bis(dimethylphosphonato)methane X1b. Amounts: x=10.4 g, y=16 mmol. Recovery after diafiltration=31% (based on P recovery); Final pH~2; GPC analysis (Superose 12 10/300 GL, 100 mM NH₄CO₃, pH=7.4, flow 1 ml/min) $R_t$=9.2 min; Composition (ICP, mole ratio): P/Si=1.1.

X2b. Amounts: x=10.4 g, y=16 mmol. Recovery after diafiltration=19% (based on P recovery); Final pH~2; GPC analysis (Superose 12 10/300 GL, 100 mM NH₄CO₃, pH=7.4, flow 1 ml/min) $R_t$=10.4 min; Composition (ICP, mole ratio): P/Si=1.1.

Example 10c

Polymerization of 50 mM 1,1-bis(triethoxysilylpropyl)-1,1-bis(dimethylphosphonato)methane X1c. Amounts: x=6.4 g, y=10 mmol. Recovery after diafiltration=21% (based on P recovery); Final pH~2; GPC analysis (Superose 12 10/300 GL, 100 mM NH₄CO₃, pH=7.4, flow 1 ml/min) $R_t$=9.7 min; Composition (ICP, mole ratio): P/Si=0.9.

X2c. Amounts: x=6.4 g, y=10 mmol. Recovery after diafiltration=25% (based on P recovery); Final pH~2; GPC analysis (Superose 12 10/300 GL, 100 mM NH₄CO₃, pH=7.4, flow 1 ml/min) $R_t$=10.5 min; Composition (ICP, mole ratio): P/Si=0.9;

Example 10d

Polymerization of 1,1-bis(triethoxysilylpropyl)-1,1-bis(dimethylphosphonato)methane to yield nanostructures X in different solvents 1,1-Bis(triethoxysilylpropyl)-1,1-bis(dimethylphosphonato)methane (3.2 g, 5 mmol) was dissolved in aqueous 80% ethylene glycol (100 ml). The reaction mixture was stirred for 21 h at 116° C. Polymerization can also be performed as above but in aqueous 80% 1,2-propanediol stirred for 24 h at 111° C. and then for 4 h at 114° C. or in aqueous 80% diethylene glycol stirred for 20 h at 108° C. and then for 2 h at 114° C. or in aqueous 80% triethylene glycol stirred for 22 h at 115° C. or in aqueous 80% di(ethylene glycol) methyl ether stirred for 18 h at 106° C. and then for 18 h at 111° C. or in aqueous 80% diethylene glycol monoethyl ether stirred for 35 h at 107° C. or in aqueous 80% glycerol stirred for 19 h at 114° C.

Example 10e

Pt-scavenging of 1,1-bis(triethoxysilylpropyl)-1,1-bis(dimethylphosphonato)methane SIR-200 (100 g, chelating resin, thiol, H form) provided by Resintech was shaken two times with aqueous 5% sodium bicarbonate solution (500 ml) and then shaken two times with MilliQ water. Water was filtered off and dry toluene (100 ml) was added to SIR-200. The volatiles were removed in vacuo and the residual water was removed by two more addition-of-toluene-vacuum cycles. 1,1-Bis(triethoxysilylpropyl)-1,1-bis(dimethylphosphonato)methane (30 g, platinum content: 39 ppm) was dissolved in dry toluene (300 ml) in a vessel. SIR-200 (10 g, treated as above) was added and then shaken overnight. SIR-200 was filtered off and the volatiles were removed in vacuo to yield a material with a platinum content of 0.38 ppm.

Example 11

Manganese Loading of Nanostructure X and Purification by Tangential Flow Filtration to Yield Nanostructures Y The pH of a solution of nanostructure X (Example 13) was adjusted from pH 2 to pH 10.4 using 6 M and 1 M NaOH (aq) and let stand for 2 h. Manganese (II) chloride tetrahydrate (xx mg, yy mmol) was then added and dissolved. The mixture was shaken for 1 h at 30° C. The pH of the mixture after the reaction was around pH 7.6, and further adjusted to pH 7.4 using 1 M HCl (aq). The reacted mixture was diluted to 50 ml with MilliQ H$_2$O and then subjected to diafiltration using 10 k NMWC pore-size column (GE Heathcare's Midgee ultra-filtration cartridge Model: UFP-10-C-3MA) to remove the free Mn ions. Alternatively, filter from Pall Life Sciences is also used specifically Centramate T-Series cassettes OS010T02 (10 k NMWC pore size cassette). The retentate was collected and the dilution & diafiltration procedure was repeatedly done three times.

Y1a. Nanostructure X used: Example X1a, 15 ml, 3.2 mmol P. MnCl$_2$ 4H$_2$O used: xx=106.7 mg, yy=0.54 mmol. Final pH 7.4; Volume particle size (DLS in 150 mM NaCl) maximum=5.6 nm; GPC analysis (Superose 12 10/300 GL, 100 mM NH$_4$CO$_3$, pH=7.4, flow 1 ml/min) R$_t$=9.5 min; Composition (ICP, mole ratio): P/Mn=5.7, P/Si=0.9, Si/Mn=6.2; Ion exchange stability at pH 5.5=45% and at pH 7=62%.

Y1b. Nanostructure X used: Example X1a, 15 ml, 3.2 mmol P. MnCl$_2$4H$_2$O used: xx=107 mg, yy=0.54 mmol. Final pH 7.4; Volume particle size (DLS in 150 mM NaCl) maximum=6.5 nm; GPC analysis (Superose 12 10/300 GL, 100 mM NH$_4$CO$_3$, pH=7.4, flow 1 ml/min) R$_t$=10.1 min & shoulder at 9 min; Composition (ICP, mole ratio): P/Mn=5.4, P/Si=0.9, Si/Mn=6; Ion exchange stability at pH 5.5=47% and at pH 7=66%.

Y2a. Nanostructure X used: Example X2a, 15 ml, 2 mmol P. MnCl$_2$ 4H$_2$O used: xx=71 mg, yy=0.36 mmol. Final pH 7.4; Volume particle size (DLS in 150 mM NaCl) maximum=4.1 nm; GPC analysis (Superose 12 10/300 GL, 100 mM NH$_4$CO$_3$, pH=7.4, flow 1 ml/min) R$_t$=10.5 min; Composition (ICP, mole ratio): P/Mn=6.6, P/Si=0.9, Si/Mn=7.3; Ion exchange stability at pH 5.5=43% and at pH 7=60%; r$_1$ at 81.33 MHz, 25° C.=41 mM$^{-1}$ Mn s$^{-1}$.

Y2b. Nanostructure X used: Example X2a, 15 ml, 2 mmol P. MnCl$_2$ 4H$_2$O used: xx=71 mg, yy=0.36 mmol. Final pH 7.4; Volume particle size (DLS in 150 mM NaCl) maximum=5.6 nm; GPC analysis (Superose 12 10/300 GL, 100 mM NH$_4$CO$_3$, pH=7.4, flow 1 ml/min) R$_t$=10.1 min; Composition (ICP, mole ratio): P/Mn=5.6, P/Si=0.9, Si/Mn=6.2; ion exchange stability at pH 5.5=44% and at pH 7=63%.

Example 11a

Polymerization of 1,1-bis(triethoxysilylpropyl)-1,1-bis(dimethylphosphonato)methane to yield nanostructures X 11a'

1,1-Bis(triethoxysilylpropyl)-1,1-bis(dimethylphosphonato)methane (0.64 g, 1 mmol) was dissolved in aqueous 80% ethylene glycol (12 ml). Sodium formate in the range from 28 mg (0.42 mmol) or 140 mg (2.1 mmol) and manganese (II) chloride tetrahydrate (33 mg, 0.17 mmol) were dissolved in aqueous 80% ethylene glycol (4 ml) each and subsequently added to the reaction mixture which was stirred for 22 h at 114° C.

11a":
1,1-Bis(triethoxysilylpropyl)-1,1-bis(dimethylphosphonato)methane (0.64 g, 1 mmol) was dissolved in aqueous 80% ethylene glycol (12 ml). Potassium formate (52 mg, 0.62 mmol) and manganese (II) chloride tetrahydrate (33 mg, 0.17 mmol) were dissolved in aqueous 80% ethylene glycol (4 ml) each and subsequently added to the reaction mixture which was stirred for 21 h at 116° C.

11a''':
1,1-Bis(triethoxysilylpropyl)-1,1-bis(dimethylphosphonato)methane (0.64 g, 1 mmol) was dissolved in aqueous 80% ethylene glycol (16 ml). Tetramethylammonium formate (30 wt. % solution in water, 0.245 ml, 0.62 mmol) and manganese (II) chloride tetrahydrate (33 mg, 0.17 mmol) dissolved in aqueous 80% ethylene glycol (4 ml) were subsequently added to the reaction mixture which was stirred for 21 h at 116° C.

Example 11b

Manganese Loading of Nanostructure X, 'Hardening' with Addition of Silanes and Purification by Diafiltration to Yield Nanostructures Z To a 2 ml solution of nanostructure X (Example 10f) was added an x ml of degassed manganese (II) chloride tetrahydrate (dissolved in 80% aqueous ethylene glycol; 100 mM) satisfying the phosphorus-manganese molar ratio of 12. An y ml of degassed sodium formate (100 mM) dissolved in 80% aqueous ethylene glycol is added to the Mn-loaded nanostructure solution fulfilling the sodium formate-manganese molar ratio of 5 or 3. The final pH is checked and adjusted to about pH 5 or 3, if necessary by adding NaOH (aq) or HCl (aq). The mixture was shaken for 12 or 18 h at 100° C. Addition of z ml of tetraethyl orthosilicate (TEOS) dissolved in ethanol (120 mM) is added to the mixture and shaked further for 18 or 24 h at 100° C. (An alternative to the post-addition of TEOS after the first heating step is the incorporation of TEOS solution directly to the Mn-loaded nanostructure solution containing Na-formate and shake for 12 or 18 h at 100° C.)

After heating and shaking, the pH was adjusted to pH 7.0±0.5 by addition of NaOH (aq), followed by ultrafiltration (UF) using a 4-ml 100 kDa centrifugal filter (Centriprep® by Millipore). The solution was first diluted with Milli-Q to about 4-ml and spin for 10-15 min (3 000×g). The filtrate was collected and transferred to a 4-ml 10 kDa centrifugal filter (Centriprep® by Millipore), diluted up to 4-ml with Milli-Q water, mixed thoroughly and spin-filtered (3 000×g, 10 min), thereafter about 500 μl retentate was collected. The dilution and diafiltration procedure was repeated three times. The final, collected 500 μl retentate was diluted to 1 ml with MilliQ water. It was followed by Mn concentration determination, Complexometric stability test evaluated by relaxometry (Example 14b), GPC analysis and composition (ICP measurement) analysis.

Z1a. 3% TEOS relative to bisbis] Nanostructure X used: 2 ml, 0.2 mmol P; x=167 μL; Na-formate-Mn ratio: 5; y=835 μL; z=25 μL final pH before heating: pH 5; GPC analysis (Superose 12 10/300 GL, 100 mM NH$_4$CO$_3$, pH=7.4, flow 1 ml/min) R$_t$=12.6 min; Composition (ICP, mole ratio): P/Mn=11.61, P/Si=1.01, Si/Mn=10.51; Complexometric stability at pH 7=24%

Z1b. 5% TEOS relative to Bisbis] Nanostructure X used: 2 ml, 0.2 mmol P; x=167 μL; Na-formate-Mn ratio: 5; y=835 μL; z=41.7 μL final pH before heating: pH 5; GPC analysis (Superose 12 10/300 GL, 100 mM NH$_4$CO$_3$, pH=7.4, flow 1 ml/min) R$_t$=12.6 min; Composition (ICP, mole ratio): P/Mn=12.05, P/Si=1.02, Si/Mn=11.77; Complexometric stability at pH 7=23%

Z1c. 3% TEOS relative to bisbis. Nanostructure X used: 2 ml, 0.2 mmol P; x=167 μL; Na-formate-Mn ratio: 5; y=835 μL; z=25 μL final pH before heating: pH 3.5; GPC analysis (Superose 12 10/300 GL, 100 mM NH$_4$CO$_3$, pH=7.4, flow 1 ml/min) R$_t$=12.6 min; Composition (ICP, mole ratio): P/Mn=13.03, P/Si=0.93, Si/Mn=13.96; Complexometric stability at pH 7=27%

Z1d. 5% TEOS relative to bisbis. Nanostructure X used: PL04064, 2 ml, 0.2 mmol P; x=167 μL; Na-formate-Mn ratio: 5; y=835 μL; z=41.7 μL final pH before heating: pH 3.5; GPC analysis (Superose 12 10/300 GL, 100 mM NH$_4$CO$_3$, pH=7.4, flow 1 ml/min) R$_t$=12.6 min; Composition (ICP, mole ratio): P/Mn=13.31, P/Si=0.92, Si/Mn=14.53; Complexometric stability at pH 7=26% pH 10.5 using 6 M and 1 M NaOH (aq) and allowed to stand for 2 h. Manganese (II) chloride tetrahydrate (45.4 mg, 0.23 mmol) was then added. The mixture was shaken for 16 h at 30° C. The pH of the mixture after the reaction was 9.3, and

TABLE 1

More examples of Mn-loaded nanostructures Y:

| | Bisbis polymer | | MnCl$_2$.4H$_2$O | | pH of Bisbis before Mn-loading | Reaction temperature (° C.) | Reaction period (h) | Nanostructure size* | | ICP Compositon | | | IEx Stability (% Mn) | | Relaxivity, r$_1$ (/mM-Mn/s) |
|---|---|---|---|---|---|---|---|---|---|---|---|---|---|---|---|
| | Volume | Amount | loaded | | | | | | | | | | | | |
| ID | (ml) | (mmol P) | mass (mg) | amount (mmol) | | | | DLS (nm) | GPC (min) | P/Mn | P/Si | Si/Mn | @ ph 5.5 | @ ph 7.0 | |
| X2a | 4 | 0.11 | 12.1 | 0.06 | 10.4 | 30 | 1 | 8.7 | 10.1 | 3.1 | 0.9 | 3.5 | 26 | 33 | 34 |
| X2a | 4 | 0.22 | 11.9 | 0.06 | 10.4 | 30 | 1 | 4.5 | 10.3 | 4.3 | 0.9 | 4.8 | 34 | 45 | 40 |
| X2a | 4 | 0.33 | 11.8 | 0.06 | 10.4 | 30 | 1 | 5.6 | 10.4 | 6.9 | 0.9 | 7.6 | 51 | 69 | 44 |
| X2a | 4 | 0.44 | 12 | 0.06 | 10.4 | 30 | 1 | 4.8 | 10.5 | 8.3 | 0.9 | 9.3 | 63 | 83 | 44 |
| X2a | 4 | 0.54 | 12 | 0.06 | 10.4 | 30 | 1 | 5.6 | 10.2 | 11.7 | 0.9 | 12.8 | 86 | 100 | 40 |
| X1b | 4 | 0.81 | 14.2 | 0.07 | 10.4 | 30 | 1 | 6.5 | | 6$^§$ | | | 71 | 88 | |
| X1b | 4 | 0.81 | 14.2 | 0.07 | 10.4 | 60 | 1 | 7.5 | 9.4 | 5.4 | 1.1 | 4.8 | 72 | 87 | 44 |
| X1b | 4 | 0.81 | 13.9 | 0.07 | 10.4 | 100 | 1 | 6.5 | | 6$^§$ | | | 80 | 84 | |
| X2b | 4 | 0.48 | 15 | 0.08 | 10.4 | 30 | 1 | 4.8 | | 6$^§$ | | | 50 | 66 | |
| X2b | 4 | 0.48 | 14.3 | 0.07 | 10.4 | 60 | 1 | 7.5 | 10.9 | 4.8 | 1 | 4.8 | 48 | 60 | 41 |
| X2b | 4 | 0.48 | 15.2 | 0.08 | 10.4 | 100 | 1 | 4.8 | | 6$^§$ | | | 52 | 66 | |
| X1b | 4 | 0.81 | 14.2 | 0.07 | 10.4 | 30 | 1 | 6.5 | | 6$^§$ | | | 71 | 88 | |
| X1b | 4 | 0.81 | 14.1 | 0.07 | 10.4 | 30 | 5 | 6.5 | | 6$^§$ | | | 62 | 78 | |
| X2b | 4 | 0.48 | 15 | 0.08 | 10.4 | 30 | 1 | 4.8 | | 6$^§$ | | | 50 | 66 | |
| X2b | 4 | 0.48 | 14.6 | 0.07 | 10.4 | 30 | 5 | 6.5 | | 6$^§$ | | | 50 | 62 | |
| X2c | 4 | 0.4 | 14.8 | 0.07 | 7 | 30 | 1 | 4.8 | | 6$^§$ | | | 36 | 53 | |
| X2c | 4 | 0.4 | 15.2 | 0.08 | 7.6 | 30 | 1 | 4.2 | | 6$^§$ | | | 39 | 54 | |
| X2c | 4 | 0.4 | 15.1 | 0.08 | 8.1 | 30 | 1 | 5.6 | | 6$^§$ | | | 36 | 53 | |
| X2c | 4 | 0.4 | 15 | 0.07 | 9.2 | 30 | 1 | 4.2 | | 6$^§$ | | | 40 | 57 | |
| X2c | 4 | 0.4 | 14.8 | 0.08 | 10.5 | 30 | 1 | | | 6$^§$ | | | 36 | 53 | |

Notes:
*1 mg/ml albumin (from chicken egg white) solution resulted to a size: DLS = 5.6 nm & GPC peak retention time = 10.3
Nanostructure size: DLS - nanostructures in 150 mM NaCl; GPC retention time - Superose 12 10/300 GL, 100 mM NH4CO3, pH = 7.4 flow 1 ml/min
$^§$Nominal values not measured; Relaxivity: Field 1.91T (81.33 MHz) @ 25 C. magnet temperature Example 12

Freeze-Dried, Formulated, Mn-Loaded Nanostructure 1,1-Bis(triethoxysilylpropyl)-1,1-bis(dimethylphosphonato)methane (6.4 g, 0.01 mmol) was dissolved in 200 ml aqueous 80% 1-propanol in a pressure vessel. The reaction mixture was stirred for 48 h at 95° C. and then 24 h at 110° C. The temperature was lowered to room temperature and the clear, colorless solution was collected. The collected solution was diluted with MilliQ H$_2$O (800 ml) and then filtered using 300 k NMWC pore-size column (GE Heathcare's Midgee ultrafiltration cartridge Model: UFP-300-C-3MA). The collected permeates (~980 ml) were then filtered using a 100 k NMWC pore size diafilter column (GE Heathcare's Midgee ultrafiltration cartridge Model: UFP-100-C-3MA) to concentrate the polymer solution. Repeated addition of MilliQ water and filtration of the collected retentate was done. Final volume of the retentate collected was about 50 ml. Composition (ICP, mole ratio): P/Si=0.84.

Furthermore, the permeate that passes through the 100 k diafilter column were collected and then filtered using a 30 k NMWC pore size diafilter column (GE Heathcare's Midgee ultrafiltration cartridge Model: UFP-30-C-3MA). Repeated addition (2 x) of MilliQ water and filtration of the collected retentate was done. Final volume of the retentate collected was about 50 ml. Composition (ICP, mole ratio): P/Si=0.88.

The pH of the nanostructure that passes through 100 k diafiltration (25 ml, 2.1 mmol) was adjusted from pH 2.2 to then adjusted to pH 7.4 using 1 M HCl (aq). The mixture was diluted to 50 ml with MilliQ H$_2$O and then subjected to diafiltration using 10 k NMWC pore-size column (GE Heathcare's Midgee ultrafiltration cartridge Model: UFP-10-C-3MA). The retentate was collected and the dilution and diafiltration procedure was repeated three times. The final collected solution volume was 10 ml.

To 8.1 ml of the collected solution, mannitol (0.36 g, 2.0 mmol) was added to reach a concentration of 250 mM. It was followed by freeze-drying for 16 h, collecting 0.5 g of white, fluffy powder. A 20 mg/ml aqueous solution of the freeze-dried material was prepared and analyzed. Particle size, volume weighted (DLS in 150 mM NaCl) maximum=4.8 m nm; GPC analysis (Superose 12 10/300 GL, 100 mM NH$_4$CO$_3$, pH=7.4, flow 1 ml/min) R$_t$=10.3 min; Composition (ICP, mole ratio): P/Mn=9.8, P/Si=0.9, Si/Mn=10.7; Ion exchange stability at pH 5.5=72% and at pH 7=89%; r$_1$ at 60 MHz, 37° C.=39 mM$^{-1}$ Mn s$^{-1}$.

Example 13

Further Purification of Nanostructure of Y Using Ion ExChange Resin

To further remove the excess or loosely bound Mn ions, the sample Y1 was treated with a cation exchanger (sulfonated polystyrene): ~10 ml of a Mn loaded nano-structure (~10 mM Mn) was mixed with 1 g of Dowex 50WX4 (Na form, pre-rinsed with water) and the pH was adjusted to 7.0 with 0.1 M NaOH. The mixture was gently rotated for 16 h and then centrifuged at 3000 rpm.

Example 14

Stability Measurement for Manganese Containing NanoStructures (Also Referred to as "Ion Exchange Stability")

First, the concentration manganese of the nanostructure solution was determine and then diluted with water to a manganese concentration of 1.5 mM and to a final volume of 2.2 ml. To 2×1.000 ml of the diluted sample solution was added 2×100 mg of Dowex 50WX4 (Na form, pre-rinsed with water). The pH was adjusted to 7.0 and 5.5 in the two solutions respectively with 0.1 M NaOH or 0.1 M HCl (usually only a few microliters are needed). The mixture was mixed well for 16 h by slowly rotating the vial. The IEX particles were allowed to settle and an aliquot of 100 µl from the supernatant take was analyzed ($[Mn]_{IEX}$). For the determination the initial concentration of manganese in the sample, the remaining solution from above was used to determine $[Mn]_{start}$. The stability was calculated as: $[Mn]_{IEX}/[Mn]_{start}*100(\%)$

Example 14b

Complexometric Stability Test for Manganese Containing Nanostructures Evaluated by Relaxometry Measure the longitudinal relaxivity of a nanostructure solution ($r_{1(ns)}$) having a concentration of 1 mM Mn. Prepare another nanostructure solution containing 1 mM Mn and add an equivalent molar amount of EDTA. The pH of this solution must be adjusted to pH 7±0.5, if necessary. Measure the longitudinal relaxivity of this nanostructure solution with added EDTA ($r_{1(ns+EDTA)}$). As a reference material, 1 mM solution using a Manganese Standard for AAS (Fluka 77036) is prepared, added an equimolar amount of EDTA, and pH adjusted to pH 7±0.5. The longitudinal relaxivity is measured ($r_{1(Mn+EDTA)}$) and resulted to a value of 1.6 mM$^{-1}$s$^{-1}$. To calculate the % Mn-released from the nanostructure after addition of equivalent EDTA:

$$\% \text{ Mn released} = 100 - \left( \frac{r_{1(ns+EDTA)} - r_{1(Mn+EDTA)}}{r_{1(ns)} - r_{1(Mn+EDTA)}} * 100 \right)$$

Note: Relaxation ($T_1$, in seconds) is measured using the Minispec mq60 NMR analyzer (60 MHz) at 37° C. and relaxivity $r_1$ is calculated using:

$$\frac{1}{T_1} = \frac{1}{T_{1H_2O}} + r_1 c_1$$

where $T_{1\,H2O}$=0.32 s; $c_1$=1 mM.

Example 15

Transmetalation with Calcium and Manganese

A buffer roughly mimicking the inorganic components of blood but without calcium was mixed from NaCl (7.14 g), NaHCO$_3$ (1.4 g), KHCO$_3$ (0.43 g), NaH$_2$PO$_4$ (0.165 g), Mg(OAc)$_2$ (0.17 g), diluted to 1.00 l volume. Henceforth designated "blood buffer". Two samples of nanostructures were tested A, (Y1, cut between 300 kDa and 100 kDa filters) and B (Y2, cut between 100 kDa and 30 kDa filters). Test tubes were prepared according to:

| | |
|---|---|
| Sample 1: 900 µl water | 100 µl of sample A |
| Sample 2: 900 µl water | 100 µl of sample B |
| Sample 3: 900 µl blood buffer | 100 µl of sample A |
| Sample 4: 900 µl blood buffer | 100 µl of sample B |
| Sample 5: 900 µl blood buffer + 1.3 mM CaCl$_2$ | 100 µl of sample A |
| Sample 6: 900 µl blood buffer + 1.3 mM CaCl$_2$ | 100 µl of sample B |

The samples mixed with A analyzed to a total Mn concentration of 1.3 mM and those of B to 1.5 mM. The solutions were incubated at room temperature for one hour and subsequently passed through a 10 kDa cut-off spin filter. The filtrates were analyzed for manganese. The results are shown in Table 2.

TABLE 2

| | % Transmetalation | | |
|---|---|---|---|
| Sample | water (pH) | Blood buffer-Ca$^{2+}$ (pH) | Blood buffer + 1.3 mM Ca$^{2+}$ (pH) |
| A | 0.1 (7.9) | 0.8 (8.0) | 2.9 (7.6) |
| B | 0.2 (7.7) | 5.2 (7.8) | 10.0 (7.6) |

Example 16

Mn-loaded dimethyl-2-(triethoxysilyl)ethylphosphonate polymer

Dimethyl-2-(triethoxysilyl)ethylphosphonate (DTEP, 0.9 g, 3.0 mmol) was dissolved in 30 ml aqueous 80% 1-propanol in a pressure vessel. The reaction mixture was stirred for 48 h at 95° C. and then for 24 h at 120° C. The temperature was lowered to room temperature and the clear, colorless solution was collected. The collected solution was diluted with MilliQ H$_2$O (470 ml) and then filtered using 100 k NMWC pore-size column (GE Heathcare's Midgee ultrafiltration cartridge Model: UFP-100-C-3MA). The collected permeates (480 ml) were then filtered using a 30 k NMWC pore size diafilter column (GE Heathcare's Midgee ultrafiltration cartridge Model: UFP-30-C-3MA) to concentrate the polymer solution. Repeated addition of MilliQ water and filtration of the collected retentate was done. Final volume of the retentate collected was about 7.5 ml. Composition (ICP, mole ratio): P/Si=0.5.

The pH of 7.5-ml DTEP polymer solution (0.4 mmol P) was adjusted from pH 2.6 to pH 10.4 using 6 M and 1 M NaOH (aq) and let stand for 2 h. Manganese (II) chloride tetrahydrate (5.9 mg, 0.3 mmol) was then added. The mixture was shaken for 1 h at 30° C. The pH of the mixture after the reaction was around pH 9.4, and then adjusted to pH 7.4 using 1 M HCl (aq). The reacted mixture was diluted to 50 ml with MilliQ H$_2$O and then subjected to diafiltration using 10 k NMWC pore-size column (GE Heathcare's Midgee ultrafiltration cartridge Model: UFP-10-C-3MA) to remove the free Mn ions. The retentate was collected and the dilution and diafiltration procedure was repeated three times. Volume weighted particle size (DLS in 150 mM NaCl) maximum=5.6 nm; GPC analysis (Superose 12 10/300 GL, 100 mM $NH_4CO_3$, pH=7.4, flow 1 ml/min); Composition (ICP, molar ratio): P/Mn=2.7, P/Si=0.5, Si/Mn=5.7; Ion exchange stability at pH 5.5=21% and at pH 7=24%; $r_1$ at 81.3 MHz, 25° C.=3 $mM^{-1}$ Mn $s^{-1}$ Example 17

Mn-Loaded Zoledronic Acid

Zoledronic acid (27 mg, 0.01 mmol) was dissolved in 10 ml MilliQ $H_2O$. A 100 mM aqueous solution of manganese (II) chloride tetrahydrate was prepared. A 10 μl of Mn-solution was mixed with 408 μl of the zoledronic acid solution and 582 μl of MilliQ $H_2O$. The pH was adjusted to 7.4 using 6 M NaOH (aq). Composition (ICP, molar ratio): P/Mn=5.26. $r_1$ at 81.3 MHz, 25° C.=2.3 $mM^{-1}$ Mn $s^{-1}$ Example 18

Mn-Loaded Methylenediphosphonic Acid

Methylenediphosphonic acid (9.2 mg, 0.05 mmol) was dissolved in 5 ml MilliQ $H_2O$. A 28 mM aqueous solution of manganese (II) chloride tetrahydrate was prepared. A 35 μl of Mn-solution is mixed with 286 μl of the methylenediphosphonic acid solution and 679 μl of MilliQ $H_2O$. The pH was adjusted to 7.1 using 6 M NaOH (aq). Composition (ICP, molar ratio): P/Mn=4.6. $r_1$ at 81.3 MHz, 25° C.=1 $mM^{-1}$ Mn $s^{-1}$.

Example 19

Other Metal Ions—Loaded into Nanostructure X

The pH of nanostructure X2a was adjusted from 2 to 10.4 using 6 M and 1 M NaOH (aq) and allowed to stand for 2 h. Metal salts (xx mg, yy mmol, se Table 3 below) such as Fe(II) chloride hydrate, Fe(III) chloride hydrate, Er(III) chloride hydrate or Dy(III) chloride hydrate was then added. The mixture was shaken for 1 h at 30° C. The pH of the mixture after the reaction varied from 4.7 to 7.2 for different samples, and was then adjusted to pH 7.4 using 1 M HCl (aq). The mixture was spin filtered (10 k MWCO, 3000×g for 15 min) and the concentrate (0.5 ml) was diluted to 4 ml using MilliQ $H_2O$. This procedure was repeated 4 times. The final concentrate was diluted to 4 ml using MilliQ $H_2O$.

a: Precursor X2a, 4 ml, 0.11 mmol P. $FeCl_2 \cdot 4H_2O$ used: xx=7.2 mg, yy=0.04 mmol. Final pH 7.4; Volume particle size (DLS in 150 mM NaCl) maximum=8.7 nm; Composition (ICP, mole ratio): P/Fe=4.2, P/Si=0.9, Si/Fe=4.5; $r_1$ at 81.33 MHz, 25° C.=3.1 $mM^{-1}$ Fe $s^{-1}$.

b: Precursor X2a, 4 ml, 0.11 mmol P. $FeCl_3 \cdot 6H_2O$ used: xx=9 mg, yy=0.03 mmol. Final pH 7.4; Volume weighted particle size (DLS in 150 mM NaCl) maximum=8.7 nm; Composition (ICP, mole ratio): P/Fe=6.5, P/Si=0.9, Si/Fe=7.2; $r_1$ at 81.33 MHz, 25° C.=8.5 $mM^{-1}$ Fe $s^{-1}$.

c: Precursor X2a, 4 ml, 0.11 mmol P. $ErCl_3 \cdot 6H_2O$ used: xx=12.7 mg, yy=0.03 mmol. Final pH 7.4; Volume weighted particle size (DLS in 150 mM NaCl) maximum=50 nm; Composition (ICP, mole ratio): P/Er=5.3, P/Si=0.9, Si/Er=5.7; $r_1$ at 81.33 MHz, 25° C.=0.4 $mM^{-1}$ Er $s^{-1}$.

d: Precursor X2a, 4 ml, 0.11 mmol P. $DyCl_3 \cdot 6H_2O$ used: xx=13.6 mg, yy=0.04 mmol. Final pH 7.4; Volume weighted particle size (DLS in 150 mM NaCl) maximum=10.1 nm; Composition (ICP, mole ratio): P/Dy=4.4, P/Si=0.9, Si/Dy=4.7; $r_1$ at 81.33 MHz, 25° C.=0.6 $mM^{-1}$ Dy $s^{-1}$.

Example 20

Relaxivity for Mn Loaded Materials

The relaxivity for some Mn loaded materials are shown in Table 3.

TABLE 3

| Sample | r1 | r2 | r2/r1 | |
|---|---|---|---|---|
| Mn-loaded Bisbis polymer | | | | |
| in H2O @ 25 C. | 44.2 | 98.9 | 2.2 | |
| in blood plasma @ 25 C. | 42.3 | 115.1 | 2.7 | * |
| in blood plasma @ 37 C. | 37.3 | 85.2 | 2.3 | * |
| with mannitol in H2O @ 25 C. | 41.2 | 94.5 | 2.3 | |
| with mannitol in blood plasma @ 37 C. | 45.5 | 127.5 | 2.8 | |
| with mannitol in blood plasma @ 25 C. | 48.1 | 164.7 | 3.4 | |
| Mn-loaded Bisbis monomer | | | | |
| in H2O @ 25 C. | 3.8 | 31.2 | 8.2 | |
| Mn-loaded DTEP polymer | | | | |
| in H2O @ 25 C. | 3 | 17.6 | 5.9 | |
| Mn-loaded Zoledronic acid | | | | |
| in H2O @ 25 C. | 2.3 | NA | NA | |
| Mn-loaded Methylenediphosphonic acid | | | | |
| in H2O @ 25 C. | 1 | NA | NA | |
| Other metal ion-loaded Bisbis polymer | | | | |
| Fe(II) in H2O @25 C. | 3.1 | 4.5 | 1.5 | |
| Fe(III) in H2O @25 C. | 8.5 | 13.4 | 1.6 | |
| Er in H2O @25 C. | 0.4 | NA | NA | |
| Dy in H2O @25 C. | 0.6 | NA | NA | |
| Mn-loaded $PEG_8$-$NH_2$-Bisbis polymer | | | | |
| in H2O @ 25 C. | 45.6 | 93.8 | 2.1 | * |
| Mn-loaded 3PEG-$NH_2$-Bisbis polymer | | | | |
| in H2O @ 25 C. | 45.1 | 98.4 | 2.2 | * |
| in blood plasma @ 25 C. | 48.1 | 164.7 | 3.4 | |
| in blood plasma @ 37 C. | 44.3 | 119.6 | 2.7 | |
| Mn-loaded PEI-bisphosphonate | | | | |
| in H2O @ 25 C. | 24.2 | 115.1 | 4.8 | |
| Mn-loaded Polyethethylenimine | | | | |
| in H2O @ 25 C. | 0.8 | NA | NA | |
| MnCl2 | | | | |
| in H2O @ 25 C. | 5.8 | nm | NA | |

Note:
Relaxivity (r) values are calculated from $(1/T1) = rc + (1/T1w)$ where c = Mn-concentration and T1w = 3.1 s
* relaxivity derived from slope of the plot of relaxation rate (1/T1) as a function of Mn concentration
Temperature: Magnet temperature; Field: 1.91 T (81.33 MHz)
r1 measured using Inversion Recovery Pulse sequence
r2 measured using Hahn Spin Echo Pulse sequence
NA: Chemical exchange contribution to r2 makes it unsuitable to be measured using Hahn Spin Echo
nm: not measured Example 21

In Vivo Imaging

The MR image quality and contrast was investigated in vivo in mice bearing the aggressively growing EL-4 mouse lymphoma. The murine lymphoma cell line EL-4 has been established from a lymphoma induced in C57BL/6 mouse. The lymphoblast cells readily grow in suspension in vitro and as allografts in C57BL/6 mice.

EL-4 cells (ECACC 85023105) were used to develop allografted tumors in C57BL/6 mice. A cell suspension was injected subcutaneously and tumors developed over a few days. Between 6-10 days after injection, tumors were used for imaging.

The MR protocol was optimized and tested in two animals. MR images were acquired in 7 animals bearing the EL-4 tumor; 4 mice received 3 mM/175 µl Y2, 3 mice received 17 mM/175 µl Magnevist, both injected during a 6 seconds period A T1-weighted GE image was acquired. The mouse was removed from the magnet and the catheter containing the contrast agent was connected. A critical point was then to inject the contrast agent rapidly, to avoid diffusion into the animal via the catheter. The pre contrast T1-weighted images were acquired and immediately thereafter the contrast agent was injected, while dynamic flash images were acquired continuously (2 pre injection, 14 post injection, 8 sec per image).

Figure 2:
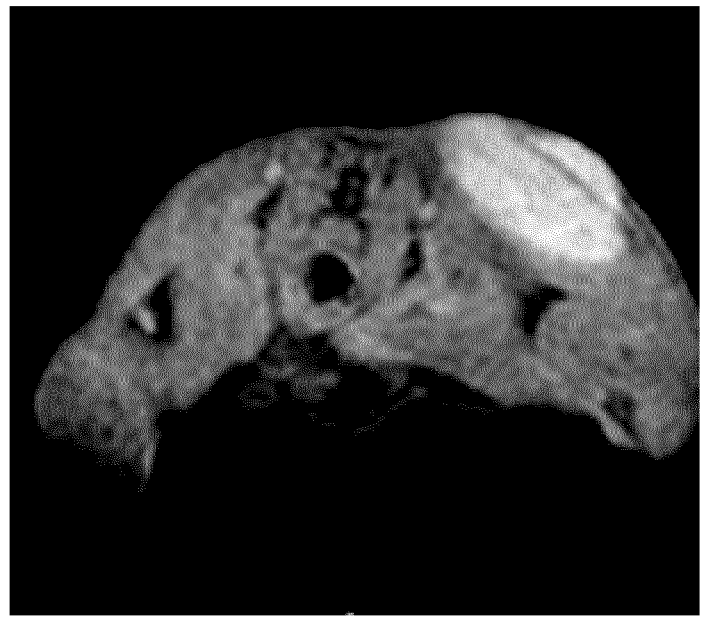
FIG. 2 illustrates contrast enhancement 5 h after injection in a mouse with a tumor.

In the experiments labeled A, B, E (see below), 10 slices with a field of view of 50×50 mm were acquired after the injection of either Y2 or Magnevist. The images acquired with 8 slices, a field of view of 50×50 mm, matrix size 256×256 and a total scan time of bit more than 10 minutes per dataset. Post contrast images were acquired every 15 minutes. From all data sets acquired after the injection of the contrast agent, 1 slice out of 10 was chosen to be representative for the enhancement, see FIG. 2.

Example 22

Synthesis of Polyethyleneimine Based Nanostructures with a Manganese Loaded 1,3-Bisphosphonate 22a: Propylene-1,3-diphosphonic acid Trimethyl silyl bromide (16.84 ml, 25.3 mmol) and tetraethylpropylene-1,3-diphosphonate (10.08 g, 31.6 mmol) were dissolved in 5 ml ice cooled dichloromethane. After 10 min. the cooling bath was removed and the mixture was stirred at room temperature for 16 hours. The volatiles were removed on a rotary evaporator. To the residue 50 ml of water was added with stirring and ice cooling. After 20 minutes the water was removed on a rotary evaporator and residual moisture was removed by first two cycles of toluene addition-evaporation and then oil-pump vacuum overnight. $^1$H-NMR showed that the ethyl groups were gone and the methylene groups were still present.

22b: Tetramethylpropylene-1,3-diphosphonate

Propylene-1,3-diphosphonic acid (600 mg) was suspended in trimethyl ortho formate (20 ml) and refluxed for 6 h whereupon 10 ml of the liquid was distilled off and the remainder left overnight. The volatiles were removed in vacuum to yield the product as an oil.

22c: 1-t-Butoxycarbonylmethyl,-O,O,O,O-tetramethylpropylene-1,3-diphosphonate

Tetramethylpropylene-1,3-diphosphonate (206 mg, 0.79 mmol) was dissolved in dry THF (5 ml) under nitrogen atmosphere and the solution was cooled in a dry ice-acetone bath. t-BuLi (2.17 M in heptane, 1.66 mmol) was syringed in and after 10 minutes t-butyl bromoacetate (0.23 ml, 1.66 mmol) was added. After 30 minutes the temperature was allowed to rise to −15° C. during 30 minutes. The reaction mixture was quenched by addition to saturated aqueous ammonium chloride. Extraction with ether (2×25 ml), drying over MgSO$_4$ and evaporation gave an oily residue. Flash chromatography on silica with dichloromethane+3% methanol gave 134 mg of the desired product.

22d: 1-Carboxylmethyl,-O,O,O,O-tetramethylpropylene-1,3-diphosphonate 1-t-Butoxycarbonyl methyl,-O,O,O,O-tetramethyl propylene-1,3-diphosphonate (150 mg) was dissolved in dichloromethane (10 ml) and trifluroacetic acid (0.5 ml) was added. The reaction mixture was left overnight and the volatiles were removed. Residual trifluoroacetic acid was removed by three cycles of toluene addition-evaporation. Yield 132 mg.

22e: Conjugation of 1-Carboxylmethyl,-O,O,O,O-tetramethylpropylene-1,3-diphosphonate to polyethyleneimine and loading with manganese 1-Carboxylmethyl,-O,O,O,O-tetramethylpropylene-1,3-diphosphonate (100 mg), polyethyleneimine (15 mg, Avg. Mw 30 000), and sulfo N-hydroxy succinimide were added to water (5 ml) and sonicated for 10 min. The pH was adjusted to 6.6 by the addition of 0.1 M NaOH. EDC was added and the solution was placed in a shaker for 19 h. Small molecular material was removed on a 20 kDa cut-off spin filter. The residue was washed 4 times on the same filter. The nanostructures measured 7.5 nm diameter when dissolved in 150 mM NaCl. To 1 ml of the above solution was added 21 mg of MnCl$_2$.4H$_2$O. The pH was adjusted to 7.3 by the addition of aqueous NaOH. The sample was washed with water 3 times on a 10 kDa nominal cut-off spinfilter. The sample was analyzed for Mn and found to be 2.4 mM. The relaxivity was found to be 18.5/mM/s at 60 MHz. The stability measured according to example 14: 0.2%.

Example 23

Conductimetric Titration of Nanostructures

Conductimetric titration can be used for the determination of the amount of $Ca^{2+}$ and $Mg^{2+}$ that can be adsorbed on nanostructures. The conductivity of a water solution of nanostructures is monitored after adding increments of a solution containing a mixture of $CaCl_2$ and $MgCl_2$. The conductivity (mS/cm) of the solution will increase at a certain rate (slope of the titration curve) as long as $Ca^{2+}$ and $Mg^{2+}$ adsorbs on the particles. When the nanostructures are saturated with $Ca^{2+}$ and $Mg^{2+}$ the conductivity will increase at another rate. For a more clear visualization of the end point (where the nanostructures are saturated with Ca and Mg), the conductivities in the presence of the nanostructures was subtracted from the conductivities obtained by adding the same increments of the Ca/Mg solution to a water.

Figure 3A:
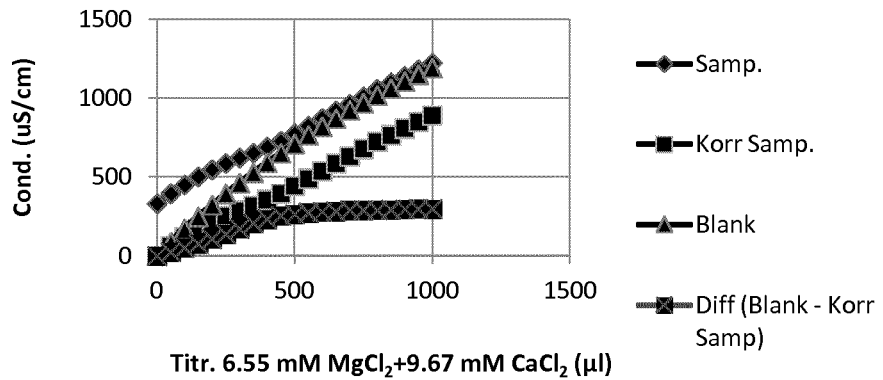
FIGS. 3a, 3b, 3c, and 3d are curves relating to conductimetric titration experiments described in example 23.

A 200 µl sample of material from example 10c ([Mn=0; [P]=138 mM) was mixed with 2300 µl water. The conductivity was measured after addition 50 µl increments of a water solution containing 6.55 mM $MgCl_2$ and 9.67 mM $CaCl_2$. (This ratio [Ca]/[Mg] is about the same as that found in blood. See "Samp." in FIG. 3a. The starting value of conductivity (no addition of Mg/Ca solution) was subtracted from "Samp." to get "Korr Samp." in FIG. 3a. Conductivity was also measured after addition of the same increments of the Mg/Ca to water to get "Blank" in FIG. 3a. Finally the conductivities from "Korr Samp." was subtracted from "Blank" to get "Diff (Blank-Korr Samp)" in the FIG. 3a.

Figure 3B:
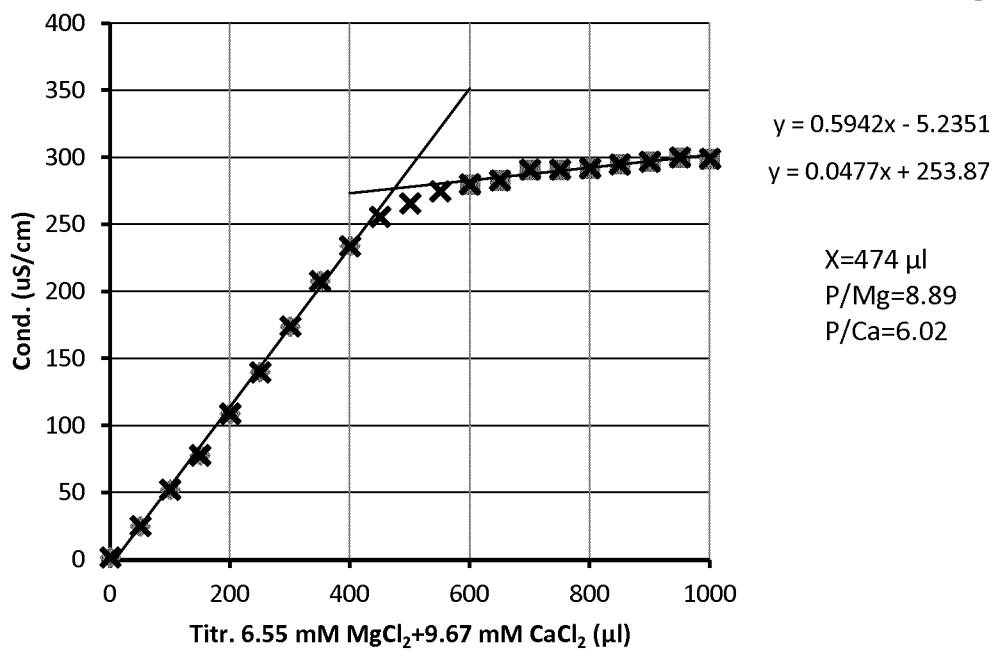

The "Diff (Blank-Korr Samp)" curve was magnified in FIG. 3b and two straight lines were fitted to the different parts of the curve. The two lines crossed at 474 µl of titrant which gives a [P]/[Mg]=8.89, [P]/[Ca]=6.02 and [P]/[Me]$_{tot}$=3.59.

Figure 3C:
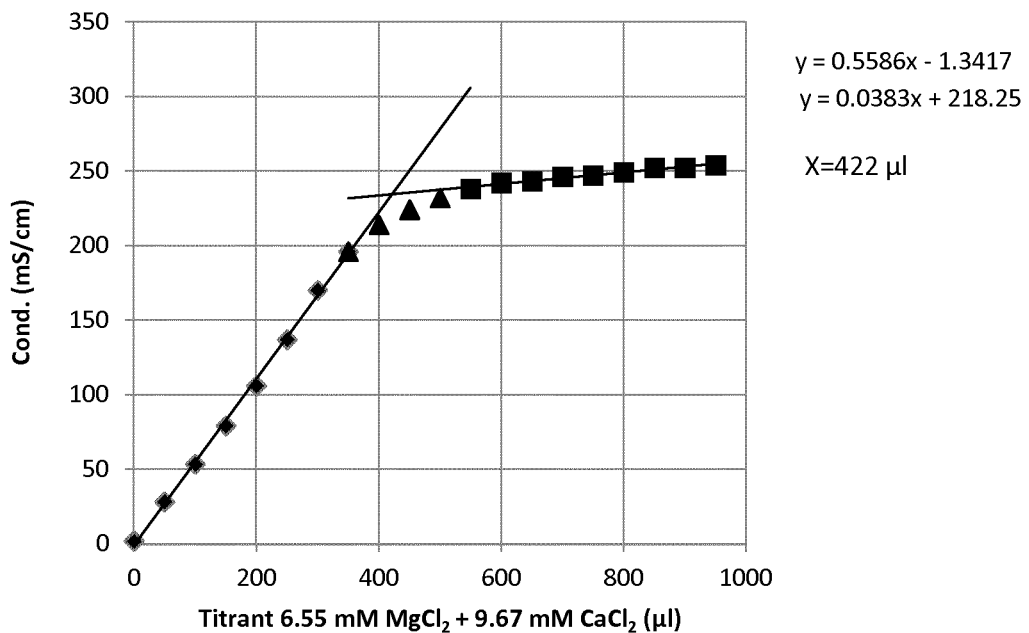

The same batch of nanostructures as above was further concentrated on a 10 kD filter (volume was reduced to about one fifth).
Titration was performed with the same corrections as above with 40 µl solution mixed with 2460 of water. The end point was determined to 422 µl. Assuming the same ratio of adsorption [P]/[Me] as the previous titration, this will give a [P]=422/474×138×0.200/0.040=613 mM. See FIG. 3c.

The main purpose of the titration was to estimate the amount of Ca/Mg solution that should be added for 90% saturation of the nanostructures.

Therefore 506 µl of a 400 mM MgCl$_2$ and 600 mM CaCl$_2$ solution was added to 14.5 ml sample solution ([P]=138 mM).

Figure 3D:
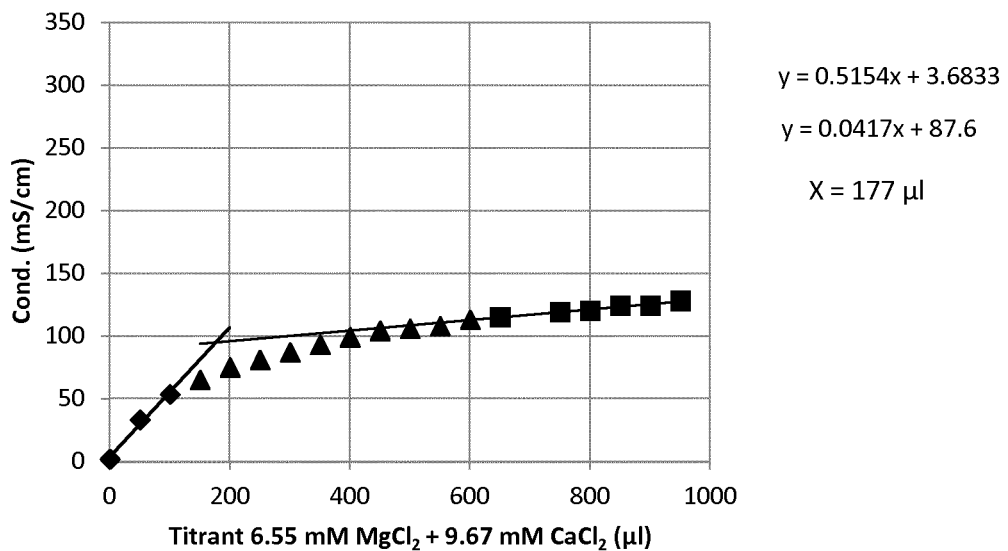

This solution was then further concentrated with a 10 kD filter as above and approximately the same amount was titrated but this time most of the sites should be occupied by metals. The results are shown in FIG. 3d.

Example 24

Formulation: Saturation with Ca and Mg Ions Followed by Mannitol Addition (Batch SI055C-PE120208)

A 2.5 ml sample of a solution of material from example 10c ([Mn]=38 mM, [P]=508 mM and Os~200 mOs/kg; Batch PE 120130) was first adjusted to physiological pH 7.4. Saturation (90%) with Ca and Mg was followed by performing the following steps. 100 µl of the solution was conductometric titrated with a Ca and Mg solution ([Ca]/[Mg]=1.48) according to the method described in Example 23 ("Conductometric Titration of Nanostructures") and the end point was determined to be when [Ca]/[Mn]=1.59 or [Mg]/[Mn]=1.08.

There was some concern that some of Mn$^{2+}$ could be displaced by Ca$^{2+}$ and Mg$^{2+}$ especially as the pH at the end of the titration was 5.5. Therefore, the solution after titration was filtered with a 10 kD filter and the amount of Mn in the filtrate was determined to contain ~15% of the total Mn in the sample. The loss of Mn from the nanostructure could at least partly be explained by the low pH at the end of the titration.

For the preparation of the corresponding Ca and Mg loaded particles 500 µl Mannitol solution (Os=280 mOs/kg) was first mixed with 21.5 µl of a concentrated Ca/Mg solution ([Ca]=600 mM, [Mg]=400 mM). This solution was then mixed with 580 µl of batch PE 120130, pH was adjusted from 6.01 to 7.40 with ~8 µl 1 M NaOH and osmolality determined to 270 mOs/kg.

Example 25

Test of Immunogenicity

Methods
A rabbit was injected 5 times with 2×0.5 ml of nanostructures according to example 24 (formulated with magnesium and calcium) at a nanostructure concentration corresponding to of 10 mg of Mn/ml. The injections were given subcutaneously, one in each of the hind legs. The nanostructures were mixed with adjuvant in the following way:
1) 1:1 v/v with Freund's Complete Adjuvant (Sigma-Aldrich) (1 ml injected in total) for primary immunization, and with Freund's Incomplete Adjuvant for booster injections
2) 1:1 (v/v) with 40 mg/ml Aluminum hydroxide (Pierce) (1 ml injected in total) for both primary immunization and booster injections Protocol for injections and serum collection:
Day 0: Collection of pre-immune serum (20 ml)
Day 0: Primary immunization
Day 14: First booster
Day 28: Second booster
Day 49: Third booster
Day 70: Fourth booster
Day 84: Collection of immune serum (60 ml)
Analysis:
1. The immunoglobulin fractions were purified from preimmune and immune sera by Protein G chromatography (GE Healthcare).
2. 2 mg of the IgG fraction was conjugated to a 2 ml agarose column (Pierce) by reductive amidation between aldehyde groups on resin and primary amine groups present on the IgG molecules. The IgG-conjugated columns were washed and equilibrated with 0.9% NaCl.
3. 100 µl of a solution of nanostructures according to example 24 corresponding to a 1.35 mM of manganese (containing approximately 21 µg of Si and 7 µg of Mn) was applied to each of the columns.
4. Flow-through: The columns were washed with 0.9% NaCl in fractions of 4×1 ml followed by 2×2 ml (fractions 1-6).
5. Eluate: Bound SI055 was eluted with 4×1 ml 1 M NaCl (fractions 7-10).
6. The flow through and eluate fractions were analyzed for Mn and Si content by ICP-AES.

Results
With both the pre-immune and immune columns, virtually all of the SI055 was detected in the flow-through. In the eluate, there was no difference between the columns in the amount of nanostructures detected.

There were no signs of irritation or other issues with the rabbit during the course of the immunization protocol.

The recovery of nanostructures in flow-through and eluate from preimmune and immune columns are shown in Table 4.

Figure 4A:
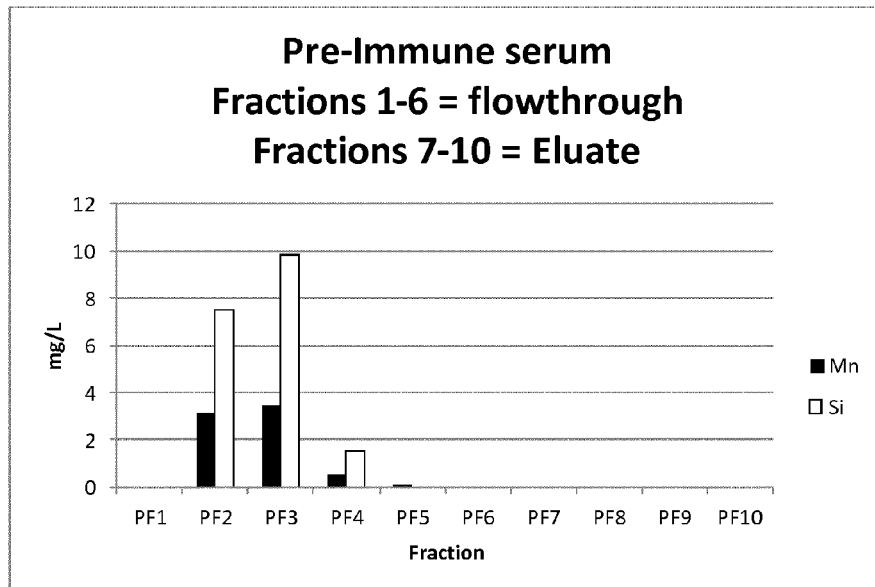
FIGS. 4a and 4b illustrates recovery of SI055 in fractions 1-10 from pre-immune (FIG. 4A) and immune columns (FIG. 4B).
Figure 4B:
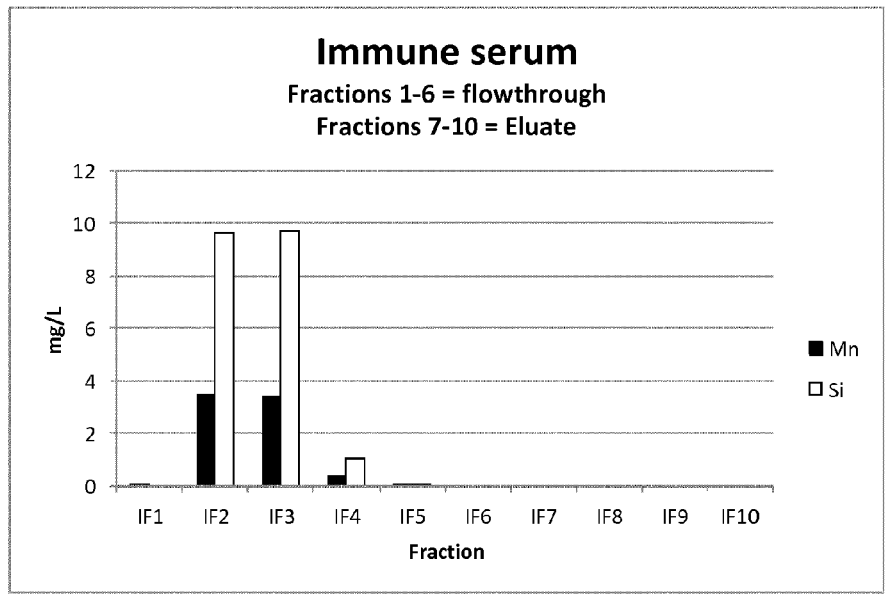

The recovery of SI055 in fractions 1-10 from pre-immune and immune columns are shown in FIGS. 4a and 4b, respectively.

TABLE 4

| | Percent of applied nanostructures | | | |
| --- | --- | --- | --- | --- |
| | Flow-through | | Eluate | |
| Column | Mn | Si | Mn | Si |
| Pre-Immune | 99.7 | 88.7 | 0.0 | 0.0 |
| Immune | 100.9 | 95.6 | 0.0 | 0.0 |

CONCLUSIONS

This example showed that there was no immune reaction towards the nanostructures in rabbits, despite a very robust immunization protocol. This result demonstrates the fact that the nanostructures are bioinert.

The invention claimed is:
1. A nanostructure comprising manganese ions incorporated in a polymeric framework comprising at least five geminal bisphosphonate groups, wherein the geminal bisphosphonate groups independently of each other are incorporated as

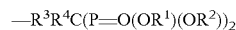

wherein:
R$^1$ and R$^2$ are independently selected from the group consisting of a negative charge, H, alkyl and aryl, and at least one of $R^3$ and $R^4$ is a group connected to the polymeric framework, or forming part of the polymeric framework, with the proviso that when only one of $R^3$ and $R^4$ is such a connected group, the other of $R^3$ and $R^4$ is either a group being able to connect to the polymeric framework, or the residue of such a group, or selected from the group consisting of H, OH, $OR^5$ and $R^5$, wherein $R^5$ is a lower alkyl.

2. A nanostructure according to claim 1, wherein the group connected to the polymeric framework, and/or the group being able to connect to the polymeric framework or the residue of such a group is selected from the group consisting of:

- $(CH_2)_n Si(R^x)_3$ wherein $R^x$ independently is a lower alkyl, OH, $O^-$, or O—, — denotes a bond to the polymeric framework, and n is 1-5,
- $(CH_2)_n COR^y$ wherein $R^y$ is O—, $NH_2$, $NHR^z$, $NR^z_2$, or a bond to the polymeric framework, $R^z$ is a lower alkyl and n is 1-5, and — denotes a bond to the polymeric framework, and
- $(CH_2)_n SO_2 R^y$ wherein $R^y$ is O—, $NH_2$, $NHR^z$, $NR^z_2$, or a bond to the polymeric framework, $R^z$ is a lower alkyl and n is 1-5 and — denotes a bond to the polymeric framework.

3. A nanostructure according to claim 1, which comprises silicon atoms.

4. A nanostructure according to claim 3, wherein the Si/Mn molar ratio is 5-20.

5. A nanostructure according to claim 1, wherein $R^3$ and/or $R^4$ are/is selected from the group consisting of —$(CH_2)_n$—$Si(R^x)_3$, wherein $R^x$ independently is a lower alkyl, OH, $O^-$, or O—, — denotes a bond to the polymeric framework, and n is 1-5.

6. A nanostructure according to claim 1, wherein the hydrodynamic diameter of the nanostructures is 3-7 nm.

7. A nanostructure according to claim 1, wherein the hydrodynamic diameter of the nanostructure is 10-20 nm.

8. A nanostructure according to claim 1, wherein the polymeric framework comprises monomer residues containing a geminal bisphosphonate group and two organo-oxysilane groups.

9. A nanostructure according to claim 1, wherein the polymeric framework is derived from polyethyleneimine.

10. A nanostructure according to claim 1, wherein the P/Mn molar ratio is 7-20.

11. A nanostructure according to claim 1, wherein said nanostructure further comprises hydrophilic groups attached to the outer parts.

12. A nanostructure according to claim 11, wherein the hydrophilic groups comprise —$(CH_2CH_2O)_n CH_3$ moieties wherein n=4-50.

13. A pharmaceutical composition comprising a nanostructure according to claim 1.

14. An MRI contrast agent comprising a pharmaceutical composition according to claim 13.

15. A method for obtaining a nanostructure according to claim 1, comprising:

obtaining nanostructures of a polymeric framework comprising geminal bisphosphonates, and contacting said nanostructures with manganese ions.

16. An MRI contrast agent comprising a nanostructure according to claim 1.

\* \* \* \* \*